(12) United States Patent
Hayoz et al.

(10) Patent No.: US 10,177,313 B2
(45) Date of Patent: *Jan. 8, 2019

(54) DIKETOPYRROLOPYRROLE POLYMERS FOR USE IN ORGANIC SEMICONDUCTOR DEVICES

(71) Applicant: BASF SE, Ludwigshafen (DE)

(72) Inventors: Pascal Hayoz, Hofstetten (CH); Olivier Aebischer, Dudingen (CH); Mathias Duggeli, Thürnen (CH); Hans Jurg Kirner, Basel (CH); Marta Fonrodona Turon, Blanes (ES)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/264,183

(22) Filed: Sep. 13, 2016

(65) Prior Publication Data

US 2017/0005270 A1    Jan. 5, 2017

Related U.S. Application Data

(60) Continuation of application No. 14/308,766, filed on Jun. 19, 2014, now Pat. No. 9,478,745, which is a
(Continued)

(30) Foreign Application Priority Data

Mar. 23, 2009  (EP) ..................... 09155919

(51) Int. Cl.
*H01L 51/00*  (2006.01)
*C07D 487/04*  (2006.01)
(Continued)

(52) U.S. Cl.
CPC ........ *H01L 51/0036* (2013.01); *C07D 487/04* (2013.01); *C07D 519/00* (2013.01); *C08G 61/124* (2013.01); *C08G 61/126* (2013.01); *C09B 57/004* (2013.01); *C09B 69/109* (2013.01); *H01B 1/127* (2013.01); *H01L 51/0035* (2013.01); *H01L 51/0043* (2013.01); *C08G 2261/124* (2013.01); *C08G 2261/1412* (2013.01); *C08G 2261/18* (2013.01); *C08G 2261/228* (2013.01); *C08G 2261/3223* (2013.01); *C08G 2261/3241* (2013.01); *C08G 2261/3243* (2013.01); *C08G 2261/334* (2013.01); *C08G 2261/598* (2013.01); *C08G 2261/91* (2013.01); *C08G 2261/92* (2013.01); *C08G 2261/94* (2013.01); *C08G 2261/95* (2013.01); *H01L 51/0003* (2013.01); *H01L 51/0053* (2013.01); *H01L 51/0558* (2013.01); *H01L 51/42* (2013.01); *Y02E 10/549* (2013.01)

(58) Field of Classification Search
CPC .............................. C08G 2261/91; H01G 4/14
See application file for complete search history.

(56) References Cited

U.S. PATENT DOCUMENTS 5,856,434 A    1/1999  Stern et al.
6,451,459 B1   9/2002  Tieke et al.
(Continued)

FOREIGN PATENT DOCUMENTS

EP    2 033 983 A2    3/2009
EP    2 034 537 A2    3/2009
(Continued)

OTHER PUBLICATIONS

English-Language Machine Translation of JP2006117591 (2006), 44 pages.
English-Language Machine Translation of JP2006295004 (2006), 22 pages.
English-Language Abstract of JP2007266285, Oct. 11, 2007.
English-Language Abstract of JP4093083, Mar. 25, 1992.
English-Language Abstract of EP 2075274, Jul. 1, 2009.
Beyerlein, T. et al., "Red electroluminescence From a 1,4-diketopyrrolo[3,4-c]pyrrole (DPP)-based Conjugated Polymer," *Synthetic Metals*, vol. 130, No. 2 (2002, ), pp. 115-119.

*Primary Examiner* — Gregory Listvoyb
(74) *Attorney, Agent, or Firm* — Marshall, Gerstein & Borun LLP

(57) ABSTRACT

The present invention relates to polymers comprising one or more (repeating) unit(s) of the formula (I) which are characterized in that $Ar^1$ and $Ar^{1'}$ are independently of each other are an annulated (aromatic) heterocyclic ring system, containing at least one thiophene ring, which may be optionally substituted by one, or more groups, and their use as organic semiconductor in organic devices, especially in organic photovoltaics (solar cells) and photodiodes, or in a device containing a diode and/or an organic field effect transistor. The polymers according to the invention have excellent solubility in organic solvents and excellent film-forming properties. In addition, high efficiency of energy conversion, excellent field-effect mobility, good on/off current ratios and/or excellent stability can be observed, when the polymers according to the invention are used in organic field effect transistors, organic photovoltaics (solar cells) and photodiodes.

(I)

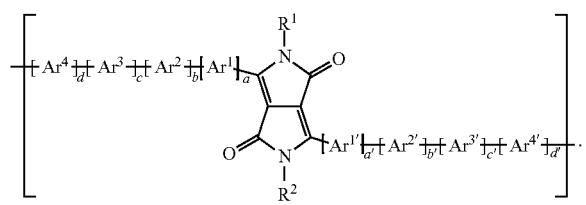

5 Claims, No Drawings

Related U.S. Application Data division of application No. 13/256,943, filed as application No. PCT/EP2010/053655 on Mar. 22, 2010, now Pat. No. 8,796,469.

(51) Int. Cl.
    *C07D 519/00*      (2006.01)
    *C08G 61/12*      (2006.01)
    *H01B 1/12*      (2006.01)
    *C09B 57/00*      (2006.01)
    *C09B 69/10*      (2006.01)
    *H01L 51/05*      (2006.01)
    *H01L 51/42*      (2006.01)

(56) References Cited

U.S. PATENT DOCUMENTS

| | | |
|---|---|---|
| 8,404,864 B2 | 3/2013 | Hao et al. |
| 8,796,469 B2 * | 8/2014 | Hayoz .................. C07D 487/04 257/40 |
| 9,478,745 B2 * | 10/2016 | Hayoz .................. C07D 487/04 |
| 2007/0228359 A1 * | 10/2007 | Heim .................. C08G 61/123 257/40 |
| 2009/0065766 A1 * | 3/2009 | Li ......................... C08G 61/12 257/40 |
| 2009/0065878 A1 | 3/2009 | Li |
| 2009/0302311 A1 | 12/2009 | Turbiez et al. |

FOREIGN PATENT DOCUMENTS

| | | |
|---|---|---|
| EP | 2 075 274 A1 | 7/2009 |
| JP | H0493083 A | 3/1992 |
| JP | 2006117591 A | 5/2006 |
| JP | 2006295004 A | 10/2006 |
| JP | 2007266285 A | 10/2007 |
| WO | WO-2004/090046 A1 | 10/2004 |
| WO | WO-2005/049695 A1 | 6/2005 |
| WO | WO-2008/000664 A1 | 1/2008 |
| WO | WO-2009/047104 A2 | 4/2009 |
| WO | WO 2009047104 * | 4/2009 |
| WO | WO-2010/049321 A1 | 5/2010 |
| WO | WO-2010/049323 A1 | 5/2010 |

\* cited by examiner

DIKETOPYRROLOPYRROLE POLYMERS FOR USE IN ORGANIC SEMICONDUCTOR DEVICES

CROSS-REFERENCE TO RELATED APPLICATIONS

This is a divisional of U.S. patent application Ser. No. 14/308,766, filed Jun. 19, 2014, now U.S. Pat. No. 9,478,745, which is a divisional of U.S. patent application Ser. No. 13/256,943, filed Oct. 5, 2011, now U.S. Pat. No. 8,796,469, which is the U.S. national phase of International Application No. PCT/EP2010/053655, filed Mar. 22, 2010, which claims priority to European Application No. 09155919.5 filed Mar. 23, 2009.

The present invention relates to polymers comprising one or more (repeating) unit(s) of the formula I, and their use as organic semiconductor in organic devices, especially in organic photovoltaics (solar cells) and photodiodes, or in a device containing a diode and/or an organic field effect transistor. The polymers according to the invention have excellent solubility in organic solvents and excellent film-forming properties. In addition, high efficiency of energy conversion, excellent field-effect mobility, good on/off current ratios and/or excellent stability can be observed, when the polymers according to the invention are used in organic field effect transistors, organic photovoltaics (solar cells) and photodiodes.

U.S. Pat. No. 6,451,459 (cf. B. Tieke et al., Synth. Met. 130 (2002) 115-119; Macromol. Rapid Commun. 21 (4) (2000) 182-189) describes diketopyrrolopyrrole based polymers and copolymers comprising the following units

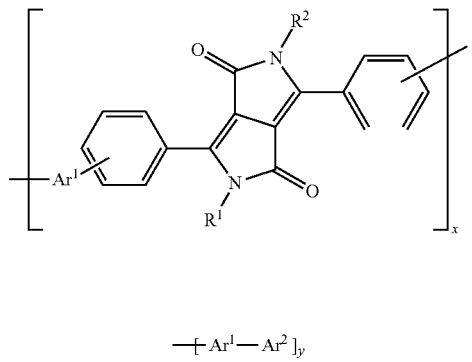

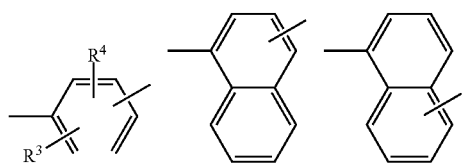

wherein x is chosen in the range of from 0.005 to 1, preferably from 0.01 to 1, and y from 0.995 to 0, preferably 0.99 to 0, and wherein x+y=1, and wherein $Ar^1$ and $Ar^2$ independently from each other stand for

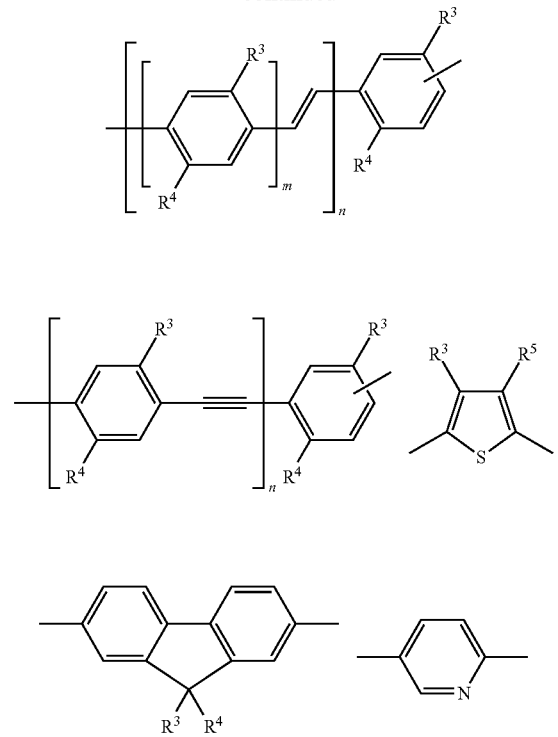

and m, n being numbers from 1 to 10, and $R^1$ and $R^2$ independently from each other stand for H, $C_1$-$C_{18}$alkyl, —C(O)O—$C_1$-$C_{18}$alkyl, perfluoro-$C_1$-$C_{12}$alkyl, unsubstituted $C_6$-$C_{12}$aryl or one to three times with $C_1$-$C_{12}$alkyl, $C_1$-$C_{12}$alkoxy, or halogen substituted $C_6$-$C_{12}$aryl, $C_1$-$C_{12}$alkyl-$C_6$-$C_{12}$aryl, or $C_6$-$C_{12}$aryl-$C_1$-$C_{12}$alkyl, $R^3$ and $R^4$ preferably stand for hydrogen, $C_1$-$C_{12}$alkyl, $C_1$-$C_{12}$alkoxy, unsubstituted $C_6$-$C_{12}$aryl or one to three times with $C_1$-$C_{12}$alkyl, $C_1$-$C_{12}$alkoxy, or halogen substituted $C_6$-$C_{12}$aryl or perfluoro-$C_1$-$C_{12}$alkyl, and $R^5$ preferably stands for $C_1$-$C_{12}$alkyl, $C_1$-$C_{12}$alkoxy, unsubstituted $C_6$-$C_{12}$aryl or one to three times with $C_1$-$C_{12}$alkyl, $C_1$-$C_{12}$alkoxy, or halogen substituted $C_6$-$C_{12}$aryl, or perfluoro-$C_1$-$C_{12}$alkyl, and their use in EL devices. The following polymer

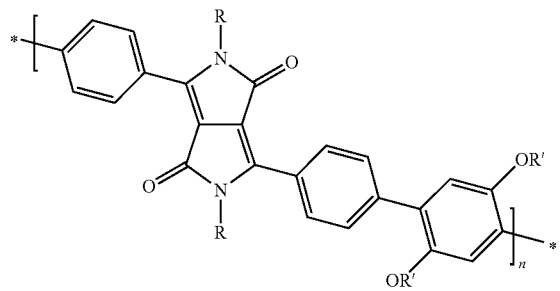

is explicitly disclosed in Tieke et al., Synth. Met. 130 (2002) 115-119. The following polymers

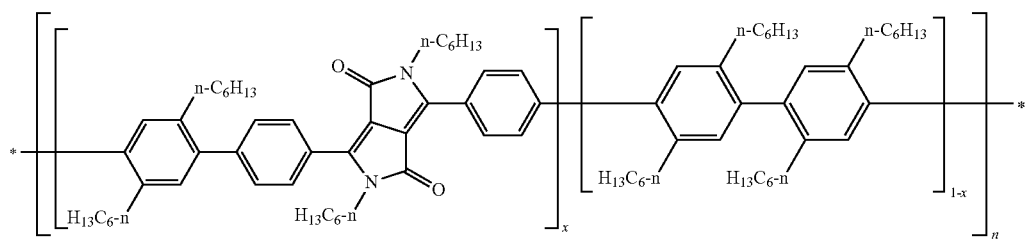

are explicitly disclosed in Macromol. Rapid Commun. 21 (4) (2000) 182-189.

WO05/049695 discloses diketopyrrolopyrrole (DPP) based polymers and their use in PLEDs, organic integrated circuits (O-ICs), organic field effect transistors (OFETs), organic thin film transistors (OTFTs), organic solar cells (O-SCs), or organic laser diodes, but falls to disclose the specific DPP based polymers of formula I.

A preferred polymer comprises a repeating unit of formula

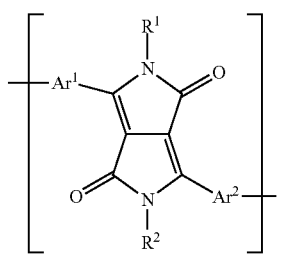

and a repeating unit

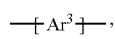

wherein
$R^1$ and $R^2$ are independently of each other a $C_1$-$C_{25}$alkyl group, especially a $C_4$-$C_{12}$alkyl group, which can be interrupted by one or more oxygen atoms, and $Ar^1$ and $Ar^2$ are independently of each other a group of formula

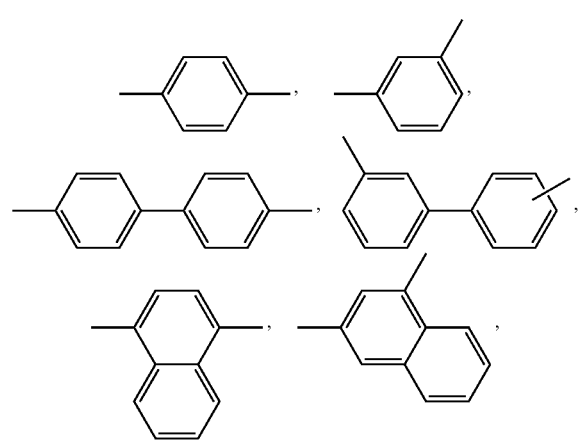

-continued

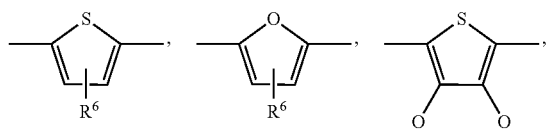

wherein —$Ar^3$— is a group of formula

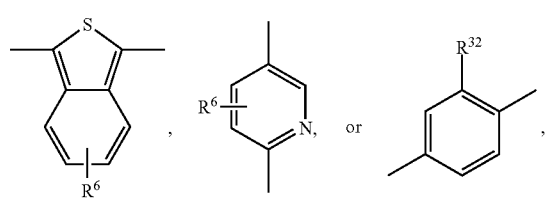

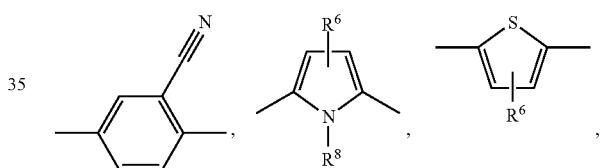

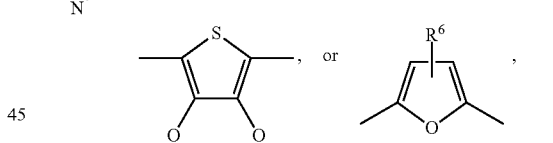

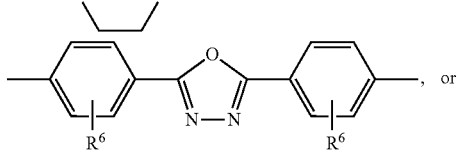

wherein
$R^6$ is hydrogen, $C_1$-$C_{18}$alkyl, or $C_1$-$C_{18}$alkoxy, and $R^{32}$ is methyl, Cl, or OMe, and $R^8$ is H, $C_1$-$C_{18}$alkyl, or $C_1$-$C_{18}$alkyl which is substituted by E and/or interrupted by D, especially $C_1$-$C_{18}$alkyl which is interrupted by —O—.

In Example 12 the preparation of the following polymer is described:

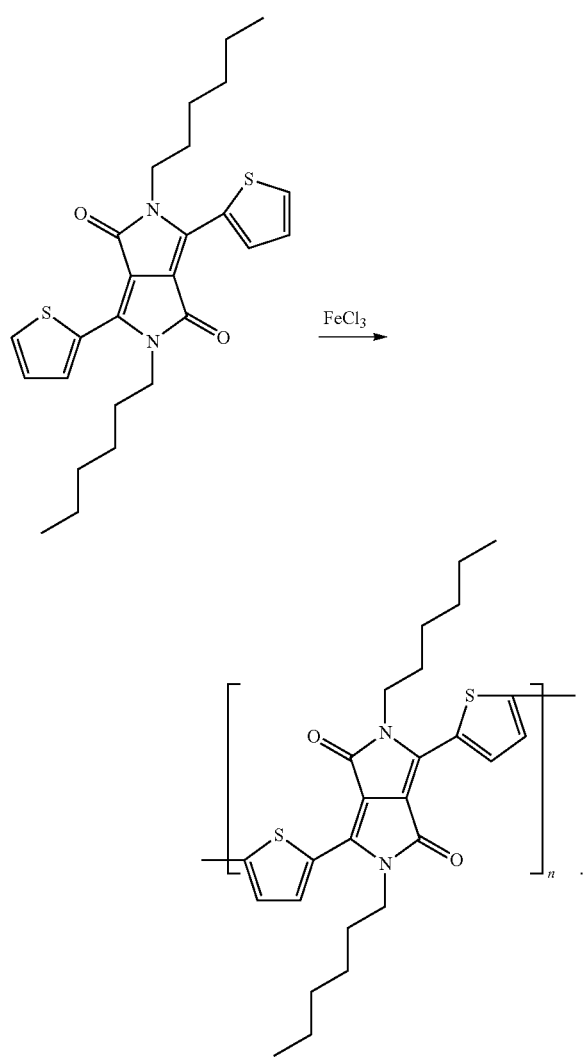

WO08/000664 describes polymers comprising (repeating) unit(s) of the formula

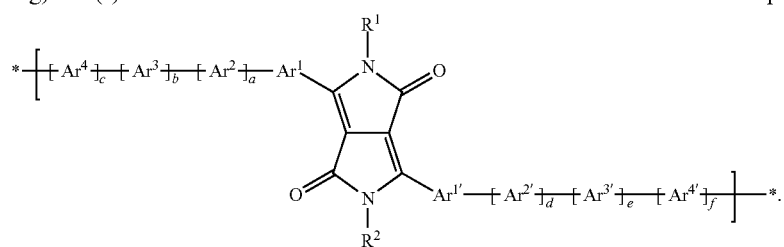

$A^1$ and $Ar^{1'}$ are preferably the same and are a group of formula

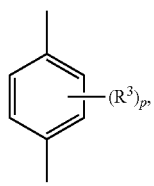

especially

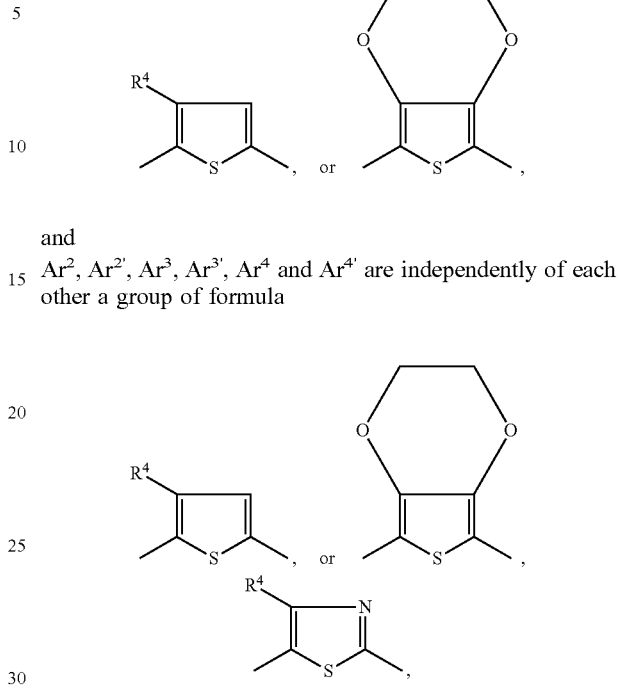

and $Ar^2$, $Ar^{2'}$, $Ar^3$, $Ar^{3'}$, $Ar^4$ and $Ar^{4'}$ are independently of each other a group of formula wherein
p stands for 0, 1, or 2, $R^3$ may be the same or different within one group and is selected from $C_1$-$C_{25}$alkyl, which may optionally be substituted by E and/or interrupted by D, or $C_1$-$C_{18}$alkoxy, which may optionally be substituted by E and/or interrupted by D;

$R^4$ is $C_6$-$C_{25}$alkyl, which may optionally be substituted by E and/or interrupted by D, $C_6$-$C_{14}$aryl, such as phenyl, naphthyl, or biphenylyl, which may optionally be substituted by G, $C_1$-$C_{25}$alkoxy, which may optionally be substituted by E and/or interrupted by D, or $C_7$-$C_{15}$aralkyl, wherein ar may optionally be substituted by G, D is —CO—, —COO—, —S—, —SO—, —SO$_2$—, —O—, —NR$^{25}$—, wherein $R^{25}$ is $C_1$-$C_{12}$alkyl, such as methyl, ethyl, n-propyl, iso-propyl, n-butyl, isobutyl, or sec-butyl;

E is —OR$^{29}$; —SR$^{29}$; —NR$^{25}$R$^{25}$; —COR$^{28}$; —COOR$^{27}$; —CONR$^{25}$R$^{25}$; or —CN; wherein $R^{25}$, $R^{27}$, $R^{28}$ and $R^{29}$ are independently of each other $C_1$-$C_{12}$alkyl, such as methyl, ethyl, n-propyl, iso-propyl, n-butyl, isobutyl, sec-butyl, hexyl, octyl, or 2-ethyl-hexyl, or $C_6$-$C_{14}$ aryl, such as phenyl, naphthyl, or biphenylyl, G has the same preferences as E, or is $C_1$-$C_{18}$alkyl, especially $C_1$-$C_{12}$alkyl, such as methyl, ethyl, n-propyl, isopropyl, n-butyl, isobutyl, sec-butyl, hexyl, octyl, or 2-ethylhexyl.

PCT/EP2009/063767 discloses polymers comprising one or more (repeating) unit(s) of the formula

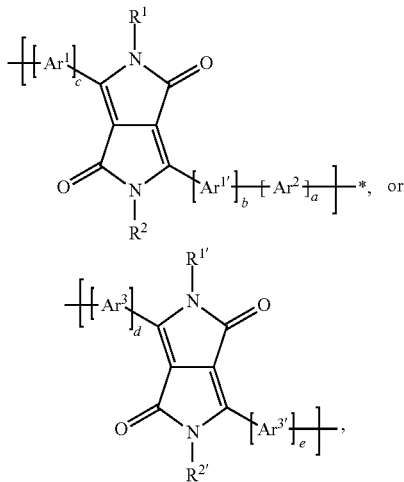

wherein
$Ar^1$, $Ar^{1'}$, $Ar^3$ and $Ar^{3'}$ are independently of each other a group of formula

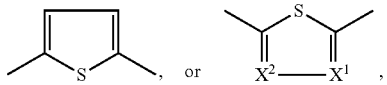

and their use as organic semiconductor in organic devices.

PCT/EP2009/063769 relates to polymers comprising one or more (repeating) unit(s) of the formula

and at least one (repeating) unit(s) which is selected from repeating units of the formula

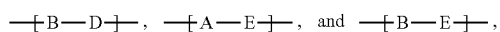

a polymer comprising one or more (repeating) unit(s) of the formula

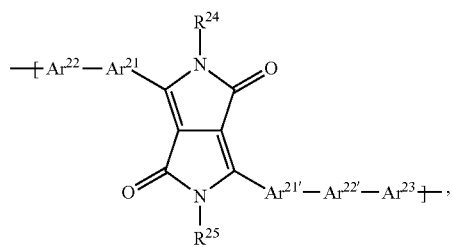

or a polymer comprising one or more (repeating) unit(s) of the formula

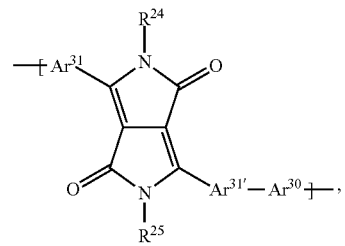

wherein A is a group of formula

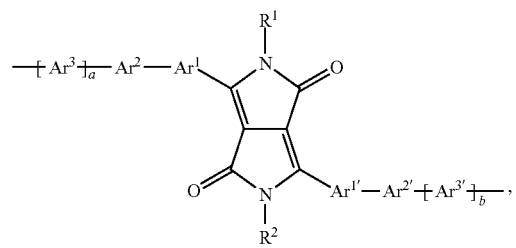

$Ar^{21}$, $Ar^{21'}$, $Ar^{31}$, $Ar^{31'}$, $Ar^1$ and $Ar^{1'}$ are independently of each other a group of formula

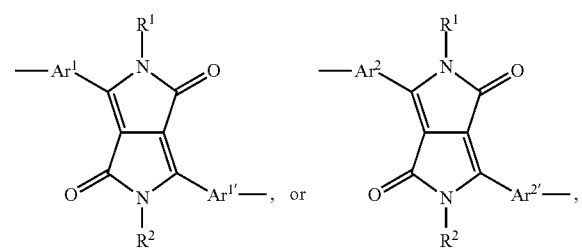

$Ar^2$, and $Ar^{2'}$ are independently of each other a group of formula

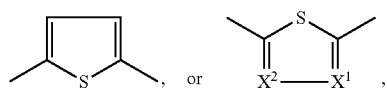

B, D and E are independently of each other a group of formula

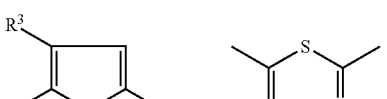

-continued

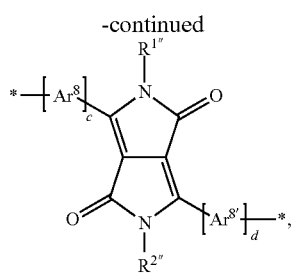

or formula

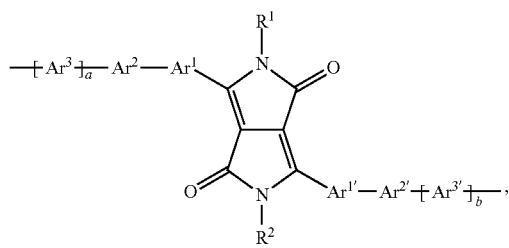

$Ar^8$ and $Ar^{8'}$ are independently of each other a group of formula

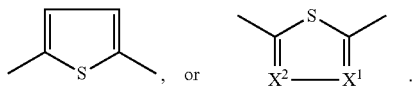

JP2007266285 relates to a field effect transistor comprising a compound represented by a formula

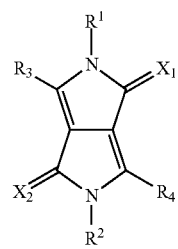 (1)

as a semiconductor material, wherein $X^1$ and $X^2$ each independently denote an oxygen atom, a sulfur atom, or a selenium atom, and $R_1$; $R_2$, $R_3$ and $R_4$ each independently denote a hydrogen atom, a substitutable aliphatic hydrocarbon group, or a substitutable aromatic group. The following DPP compound is explicitly disclosed:

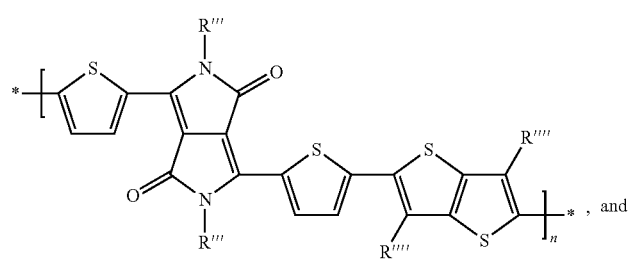

EP2034537A2 is directed to a thin film transistor device comprising a semiconductor layer, the semiconductor layer comprising a compound comprising a chemical structure represented by:

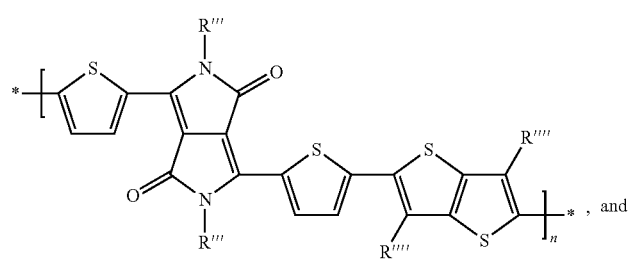

wherein each X is independently selected from S, Se, O, and NR", each R" is independently selected from hydrogen, an optionally substituted hydrocarbon, and a hetero-containing group, each Z is independently one of an optionally substituted hydrocarbon, a hetero-containing group, and a halogen, d is a number which is at least 1, e is a number from zero to 2; a represents a number that is at least 1; b represents a number from 0 to 20; and n represents a number that is at least 1.

Among others the following polymers are explicitly disclosed:

(48)

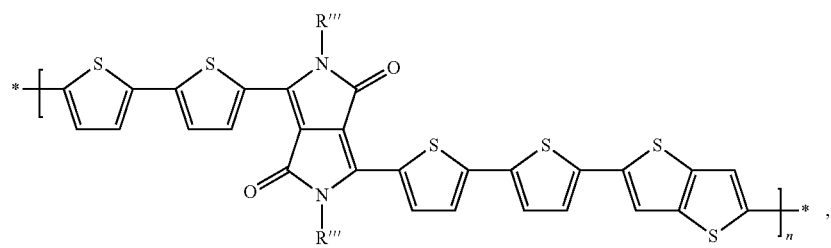

, and (49)

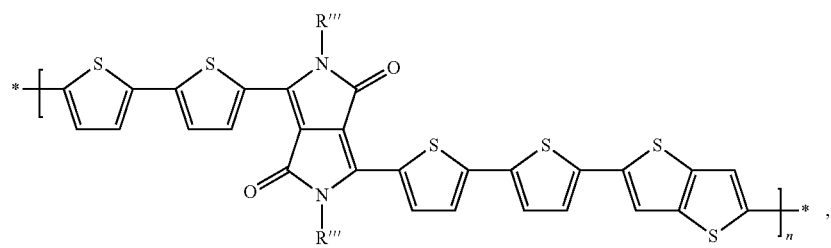

,

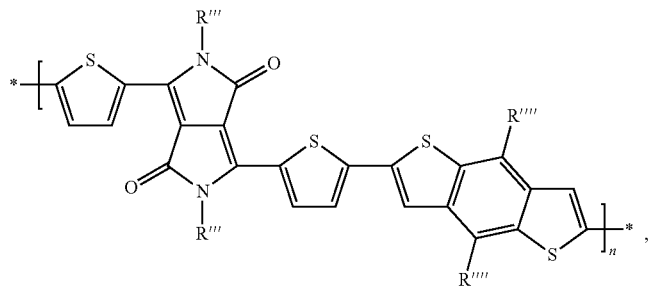

(50)

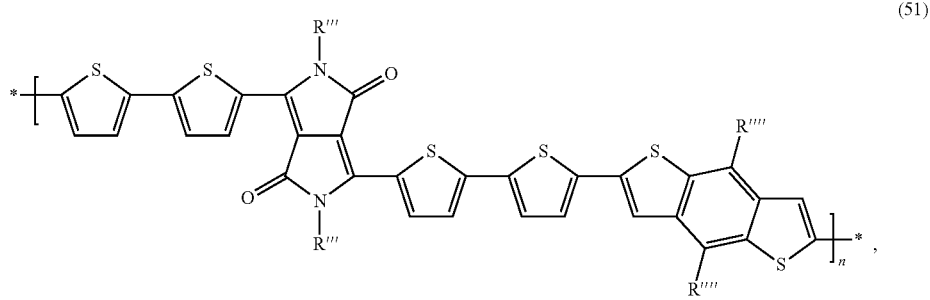

(51)

wherein n is the number of repeat units and can be from about 2 to about 5000, R''' and R'''' can be the same or different substituent, and wherein the substituent is independently selected from the group consisting of an optionally substituted hydrocarbon group and a heteroatom-containing group.

EP2075274A1, which enjoys an earlier priority date (27 Dec. 2007) than the present invention (May 12, 2008), but has been published (Jan. 7, 2009) after the priority date of the present invention, discloses a soluble polythiophene derivative containing highly coplanar repeating units. The coplanar characteristic of the TPT (thiophene-phenylene-thiophene) units improves the degree of intramolecular conjugation and intermolecular π-π interaction.

The production of the following polymer by Stille Coupling Polymerisation is described in Example 12 of EP2075274A1:

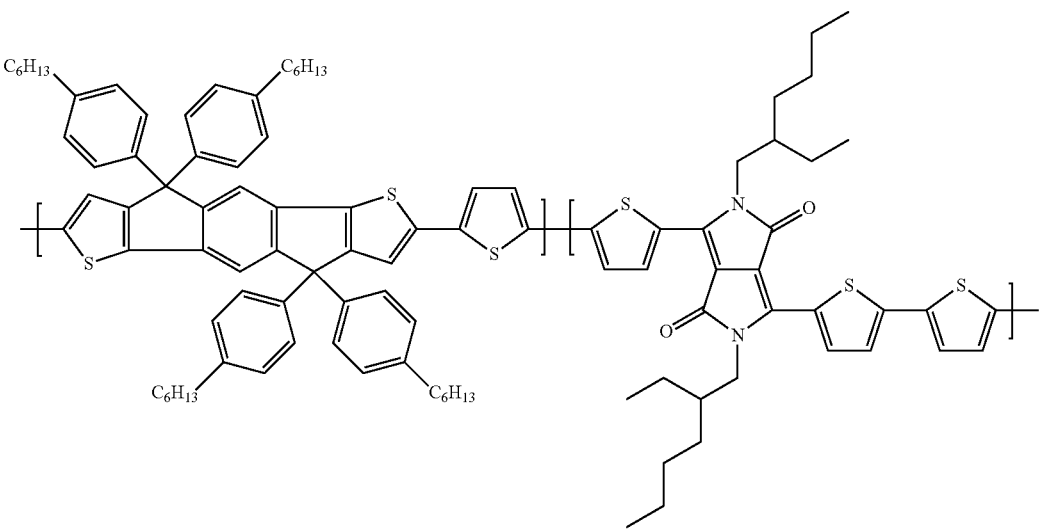

(molecular weight: 28589 g/mol).

It is the object of the present invention to provide polymers, which show high efficiency of energy conversion, excellent field-effect mobility, good on/off current ratios and/or excellent stability, when used in organic field effect transistors, organic photovoltaics (solar cells) and photodiodes.

Said object has been solved by polymers comprising one or more (repeating) unit(s) of the formula

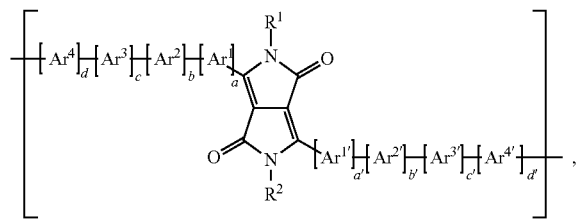
(I)

wherein a is 1, 2, or 3; a' is 0, 1, 2, or 3; b is 0, 1, 2, or 3; b' is 0, 1, 2, or 3; c is 0, 1, 2, or 3; c' is 0, 1, 2, or 3; d is 0, 1, 2, or 3; d' is 0, 1, 2, or 3; with the proviso that b' is not 0, if a' is 0; $R^1$ and $R^2$ may be the same or different and are selected from hydrogen, a $C_1$-$C_{100}$alkyl group, —COOR$^{103}$, a $C_1$-$C_{100}$alkyl group which is substituted by one or more halogen atoms, hydroxyl groups, nitro groups, —CN, or $C_6$-$C_{18}$aryl groups and/or interrupted by —O—, —COO—, —OCO—, or —S—; a $C_7$-$C_{100}$arylalkyl group, which can be substituted one to three times with $C_1$-$C_8$alkyl and/or $C_1$-$C_8$alkoxy; a carbamoyl group, $C_5$-$C_{12}$cycloalkyl, which can be substituted one to three times with $C_1$-$C_8$alkyl and/or $C_1$-$C_8$alkoxy; a $C_6$-$C_{24}$aryl group, in particular phenyl or 1- or 2-naphthyl, which can be substituted one to three times with $C_1$-$C_8$alkyl, $C_1$-$C_8$thioalkoxy, and/or $C_1$-$C_8$alkoxy, or pentafluorophenyl, $Ar^1$ and $Ar^{1'}$ are independently of each other are an annulated (aromatic) heterocyclic ring system, containing at least one thiophene ring, which may be optionally substituted by one, or more groups, $Ar^2$, $Ar^{2'}$, $Ar^3$, $Ar^{3'}$, $Ar^4$ and $Ar^{4'}$ have the meaning of $Ar^1$, or are independently of each other

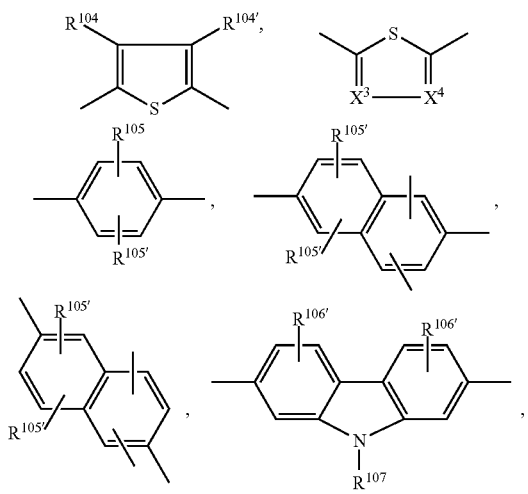

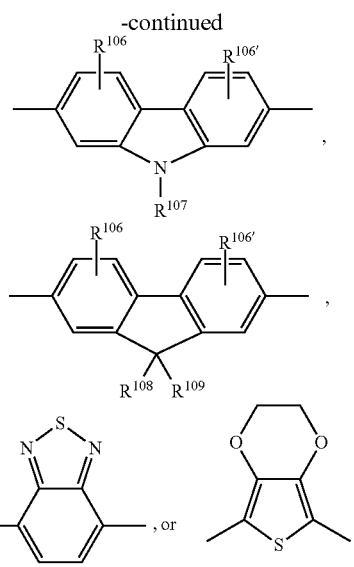

wherein one of $X^3$ and $X^4$ is N and the other is $CR^{99}$,
$R^{99}$, $R^{104}$ and $R^{104'}$ are independently of each other hydrogen, halogen, especially F, or a $C_1$-$C_{25}$alkyl group, especially a $C_4$-$C_{25}$alkyl, which may optionally be interrupted by one or more oxygen or sulphur atoms, a $C_7$-$C_{25}$aralkyl group, or a $C_1$-$C_{25}$alkoxy group,
$R^{105}$, $R^{105'}$, $R^{106}$ and $R^{106'}$ are independently of each other hydrogen, halogen, $C_1$-$C_{25}$alkyl, which may optionally be interrupted by one or more oxygen or sulphur atoms, $C_7$-$C_{25}$aralkyl, or $C_1$-$C_{18}$alkoxy,
$R^{107}$ is $C_7$-$C_{25}$aralkyl, $C_6$-$C_{18}$aryl; $C_6$-$C_{18}$aryl which is substituted by $C_1$-$C_{18}$alkyl, $C_1$-$C_{18}$perfluoroalkyl, or $C_1$-$C_{18}$alkoxy; $C_1$-$C_{18}$alkyl; $C_1$-$C_{18}$alkyl which is interrupted by —O—, or —S—; or —COOR$^{103}$; $R^{103}$ is $C_1$-$C_{50}$alkyl, especially $C_4$-$C_{25}$alkyl;
$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$aralkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{108}$ and $R^{109}$ together form a group of formula =$CR^{110}R^{111}$, wherein
$R^{110}$ and $R^{111}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or
$R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl,
D is —CO—, —COO—, —S—, —O—, or —NR$^{112}$—,
E is $C_1$-$C_8$thioalkoxy, $C_1$-$C_8$alkoxy, CN, —NR$^{112}$R$^{113}$, —CONR$^{112}$R$^{113}$, or halogen,
G is E, or $C_1$-$C_{18}$alkyl, and
$R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—.

Most preferably $R^{104}$, $R^{104'}$, $R^{105}$, $R^{105'}$, $R^{106}$, $R^{106'}$, $R^{107}$, $R^{108}$, $R^{109}$ are independently of each other hydrogen, or $C_1$-$C_{24}$alkyl.

Advantageously, the polymer of the present invention, or an organic semiconductor material, layer or component, comprising the polymer of the present invention can be used in organic photovoltaics (solar cells) and photodiodes, or in an organic field effect transistor (OFET).

The term polymer comprises oligomers as well as polymers. The oligomers of this invention have a weight average molecular weight of <4,000 Daltons. The polymers of this invention preferably have a weight average molecular weight of 4,000 Daltons or greater, especially 4,000 to 2,000,000 Daltons, more preferably 10,000 to 1,000,000 and most preferably 10,000 to 100,000 Daltons. Molecular weights are determined according to high-temperature gel permeation chromatography (HT-GPC) using polystyrene standards. The polymers of this invention preferably have a polydispersity of 1.01 to 10, more preferably 1.1 to 3.0, most preferred 1.5 to 2.5.

An annulated (aromatic) heterocyclic ring system, containing at least one thiophene ring, means an annulated hetero-2-, -3-, -4-, -5-, -6- etc. ring system, which comprises at least one thiophene ring and which may be optionally substituted by one, or more groups. That is, the term "annulated" means that the hetero ring system consists of a thiophene ring and at least one further aromatic, or heteroaromatic ring. The discrete rings can be aromatic, or heteroaromatic. The hetero ring system contains preferably 1, 2, 3, or 4 thiophene rings. In a preferred embodiment of the present invention the hetero ring system comprises at least two thiophene rings. In another preferred embodiment of the present invention the bonding to the DPP skeleton and another repeating unit is effected via two different rings of the annulated (aromatic) heterocyclic ring system.

Examples of annulated (aromatic) heterocyclic ring systems are the groups of formula Xa to Xz and XIa to XIm mentioned below:

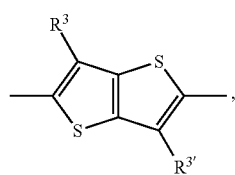
(Xa)

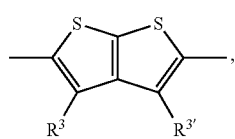
(Xb)

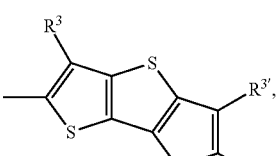
(Xc)

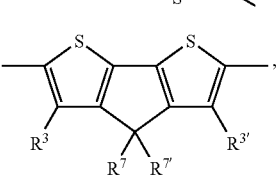
(Xd)

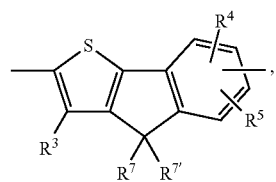
(Xe)

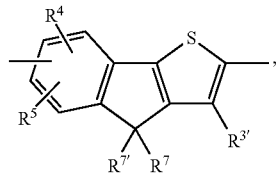
(Xf)

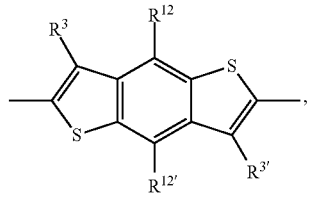
(Xg)

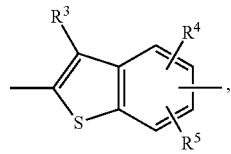
(Xh)

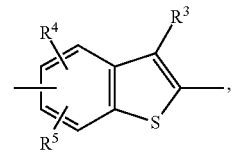
(Xi)

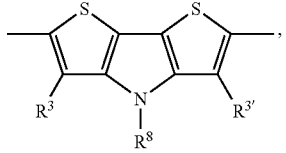
(Xj)

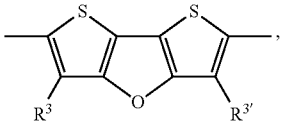
(Xk)

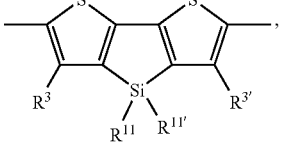
(Xl)

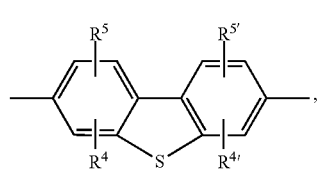
(Xm)

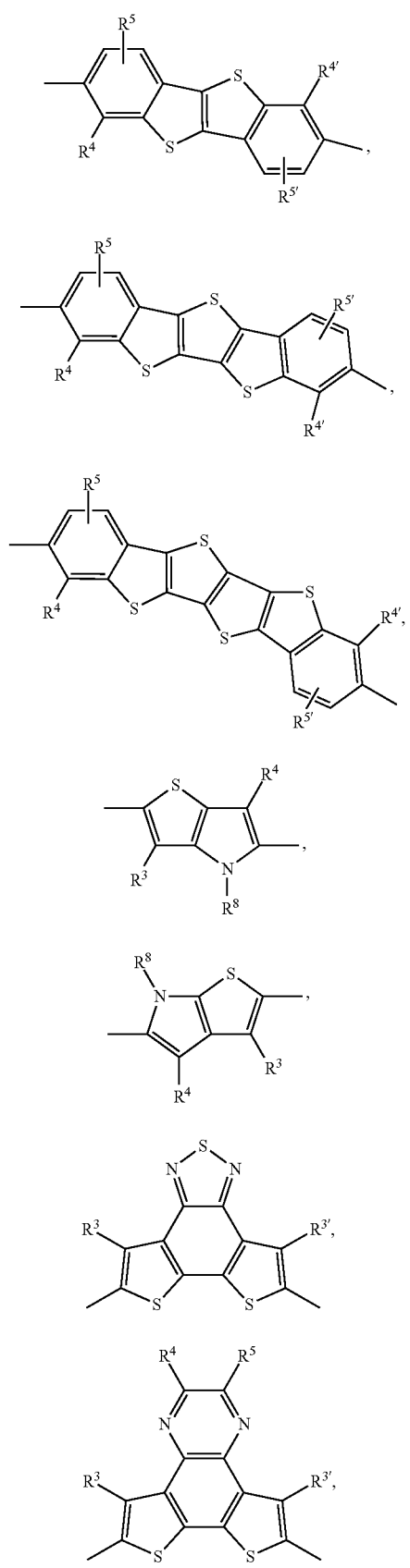
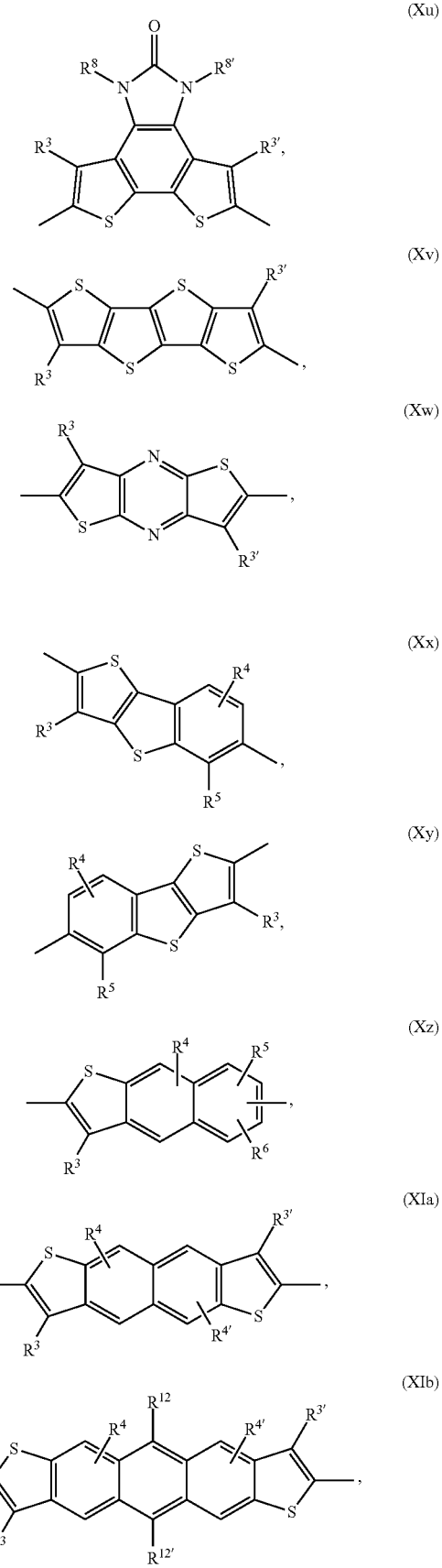

-continued

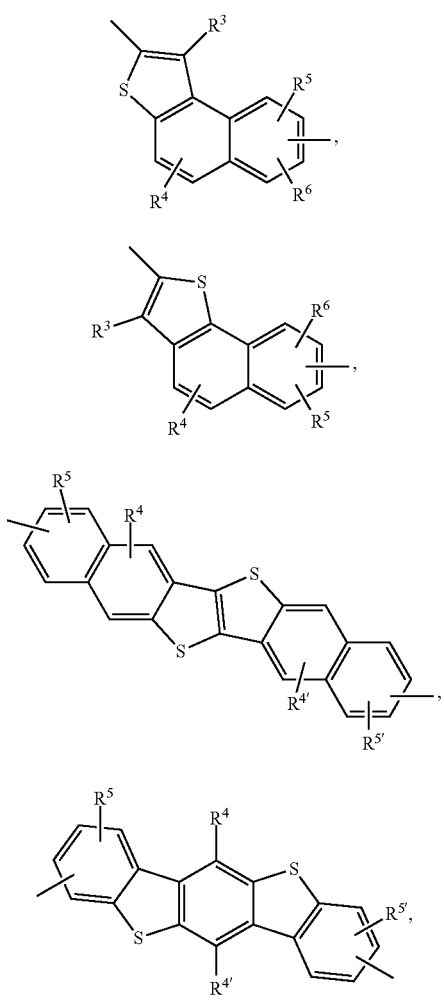

(XIc)

(XId)

(XIe)

(XIf)

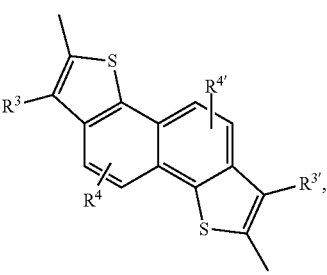

(XIg)

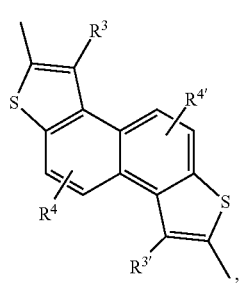

(XIh)

-continued

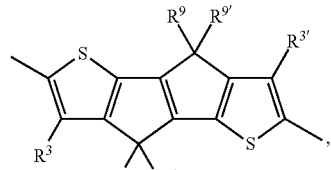

(XIi)

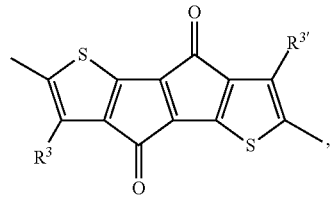

(XIj)

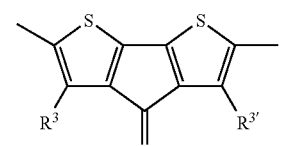

(XIk)

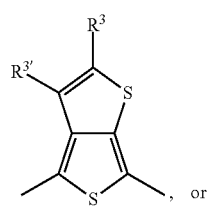

(XIl)

, or (XIm)

wherein
R³ and R³' are independently of each other hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;
R⁴, R⁴', R⁵, R⁵', R⁶ and R⁶' are independently of each other hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;
R¹¹⁴ is $C_1$-$C_{25}$alkyl, especially $C_4$-$C_{25}$alkyl, which may optionally be interrupted by one, or more oxygen, or sulphur atoms,
R⁷, R⁷', R⁹ and R⁹' are independently of each other hydrogen, $C_1$-$C_{25}$alkyl, especially $C_4$-$C_{25}$alkyl, which may optionally be interrupted by one, or more oxygen, or sulphur atoms, or $C_7$-$C_{25}$aralkyl,
R⁸ and R⁸' are independently of each other hydrogen, $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_4$-$C_{25}$alkyl, which may optionally be interrupted by one or more oxygen or sulphur atoms;
R¹¹ and R¹¹' are independently of each other $C_1$-$C_{25}$alkyl group, especially a $C_1$-$C_{18}$alkyl group, or a phenyl group, which can be substituted one to three times with $C_1$-$C_8$alkyl and/or $C_1$-$C_8$alkoxy;

$R^{12}$ and $R^{12'}$ are independently of each other hydrogen, halogen, $C_1$-$C_{25}$alkyl, especially $C_4$-$C_{25}$alkyl, which may optionally be interrupted by one, or more oxygen, or sulphur atoms, $C_7$-$C_{25}$aralkyl, $C_1$-$C_{25}$alkoxy, or

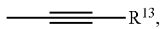

wherein $R^{13}$ is a $C_1$-$C_{10}$alkyl group, or a tri($C_1$-$C_8$alkyl)silyl group.

In a preferred embodiment of the present invention the annulated (aromatic) heterocyclic ring system is selected from groups of formula Xa, Xb, Xc, Xd, and Xg. In another preferred embodiment of the present invention the annulated (aromatic) heterocyclic ring system is selected from groups of formula Xe, Xf, Xh, Xi, Xj, Xk, Xm, Xn, Xq, Xr, Xv, Xx, Xy, XIa, XIb, XIg, XIh, Xii and XII.

$R^1$ and $R^2$ can be different, but are preferably the same. Preferably, $R^1$ and $R^2$ independently from each other stand for $C_1$-$C_{100}$alkyl, $C_5$-$C_{12}$cycloalkyl, which can be substituted one to three times with $C_1$-$C_8$alkyl and/or $C_1$-$C_8$alkoxy, phenyl or 1- or 2-naphthyl which can be substituted one to three times with $C_1$-$C_8$alkyl and/or $C_1$-$C_8$alkoxy, or —$CR^{101}R^{102}$—$(CH_2)_m$-$A^3$, wherein $R^{101}$ and $R^{102}$ stand for hydrogen, or $C_1$-$C_4$alkyl, $A^3$ stands for phenyl or 1- or 2-naphthyl, which can be substituted one to three times with $C_1$-$C_8$alkyl and/or $C_1$-$C_8$alkoxy, and m stands for 0 or 1. $R^1$ and $R^2$ are more preferably a $C_8$-$C_{36}$ alkyl group, especially a $C_{12}$-$C_{24}$alkyl group, such as n-dodecyl, tridecyl, tetradecyl, pentadecyl, hexadecyl, 2-ethylhexyl, 2-butyl-hexyl, 2-butyl-octyl, 2-hexyldecyl, 2-decyltetradecyl, heptadecyl, octadecyl, eicosyl, heneicosyl, docosyl, or tetracosyl. In a particularly preferred embodiment of the present invention $R^1$ and $R^2$ are a 2-hexyldecyl, or 2-decyl-tetradecyl group.

Advantageously, the groups $R^1$ and $R^2$ can be represented by formula

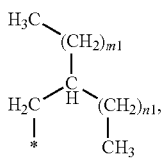

wherein m1=n1+2 and m1+n1≤24. Chiral side chains, such as $R^1$ and $R^2$, can either be homochiral, or racemic, which can influence the morphology of the polymers.

Preferably a is 1, a' is 1; b is 0, or 1; b' is 0, or 1; c is 0, or 1; c' is 0, or 1; d is 0, 1, 2, or 3; d' is 0, 1, 2, or 3. If a' is 0, b' is not 0. Examples of groups wherein d, or d' are 2, or 3 are shown below:

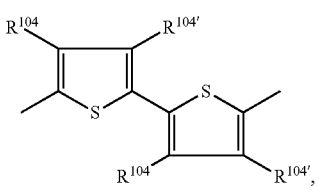

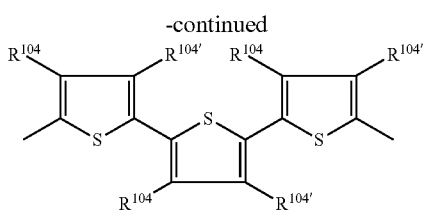

If a substituent, such as, for example $R^{104}$ and $R^{104'}$, occurs more than one time in a group, it can be different in each occurrence.

As indicated by the formula

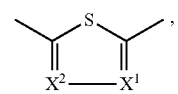

the group

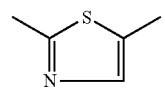

can be arranged in the polymer chain in two ways

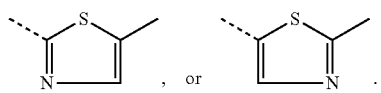

The notation

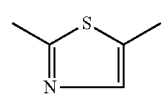

should comprise both possibilities. The same applies for other groups, which can be arranged in different ways in the monomer and/or polymers.

The groups

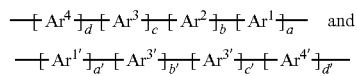

can be different, but are preferably the same. In the preferred compounds Ia to Iv mentioned below the group

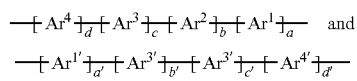

are the same. In principal, said groups may be different, which in case of compound Ia may result in compound

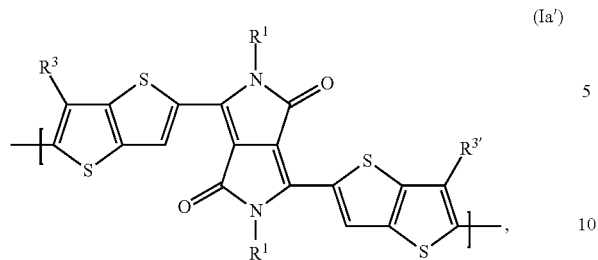
(Ia')
which according to the present invention is less preferred.
In a preferred embodiment of the present invention the polymer comprises one or more (repeating) unit(s) of the formula
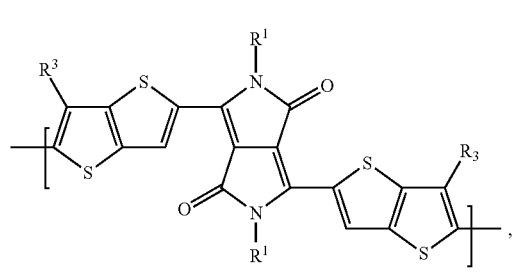
(Ia)
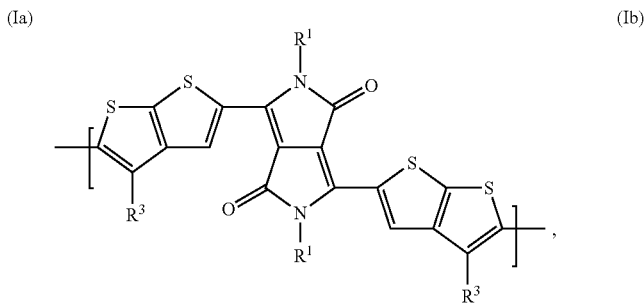
(Ib)
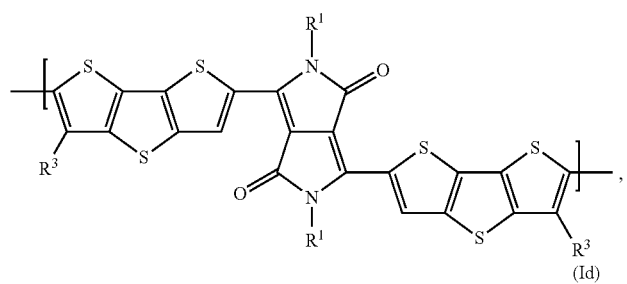
(Ic)
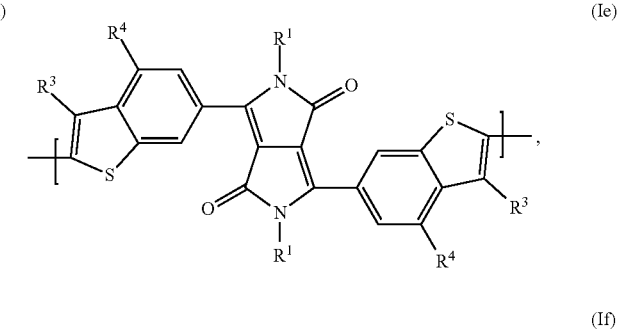
(Ie)
(Id)
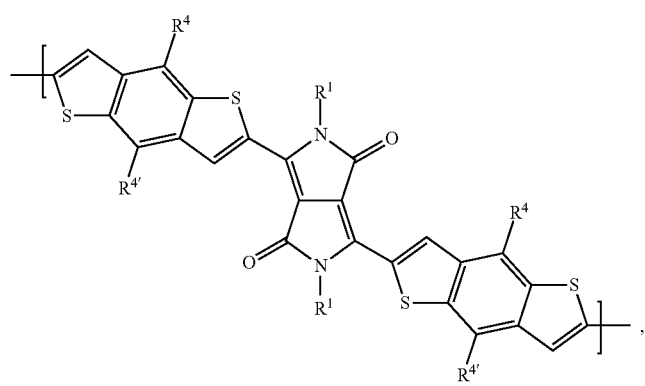
(If)

-continued
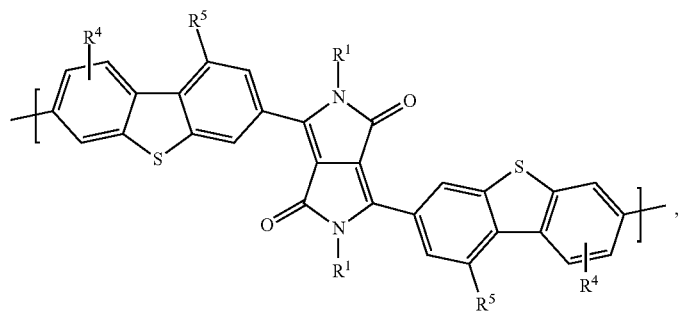 (Ig)
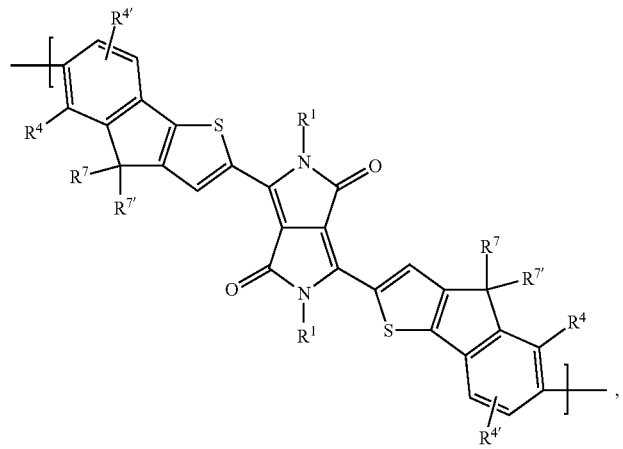 (Ih)
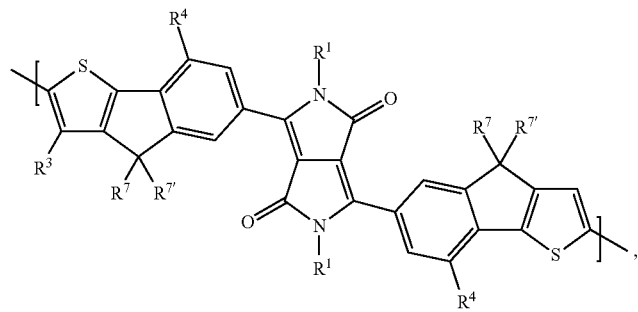 (Ii)
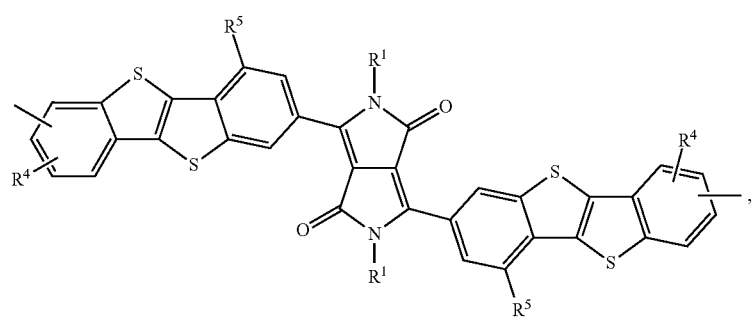 (Ij)
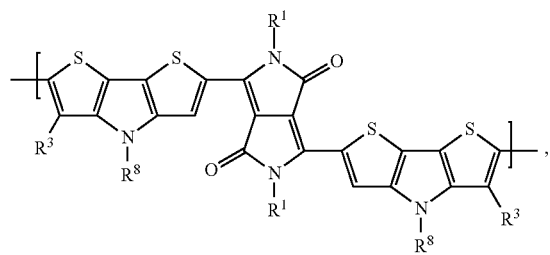 (Ik)
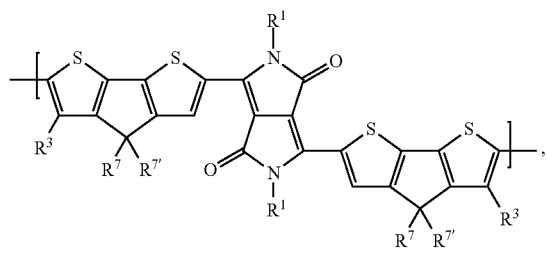 (Il)

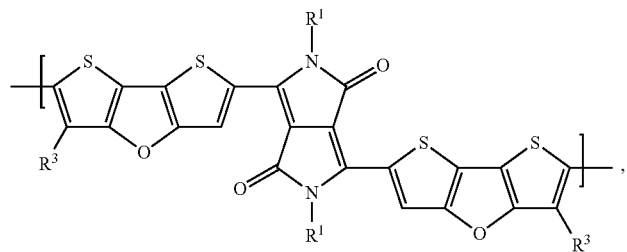
(Im)
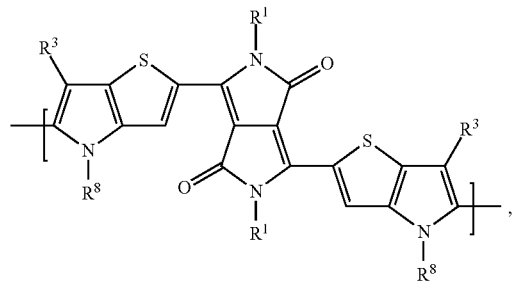
(In)
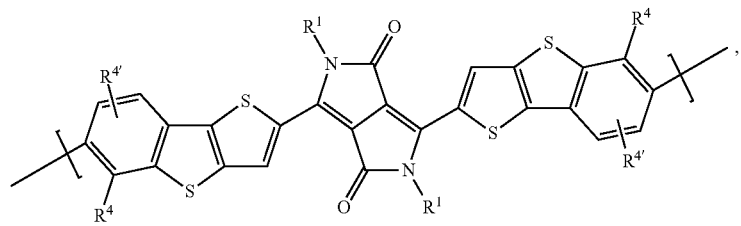
(Io)
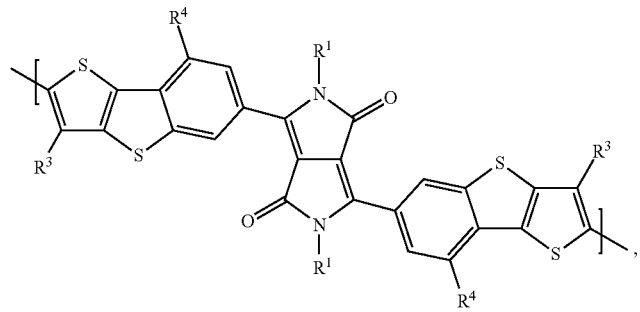
(Ip)
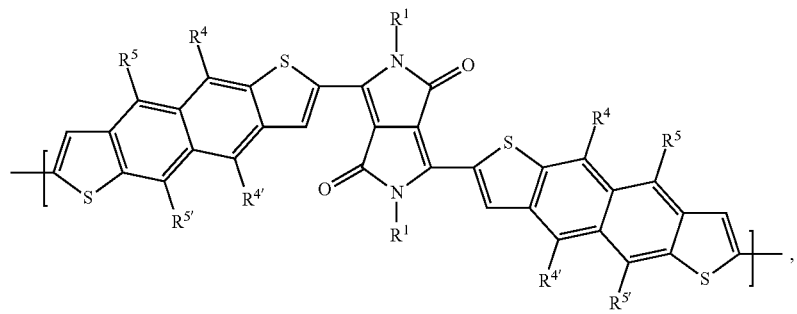
(Iq)

-continued
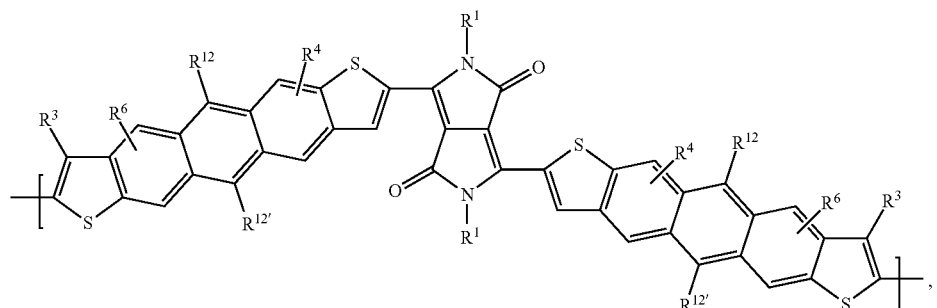
(Ir)
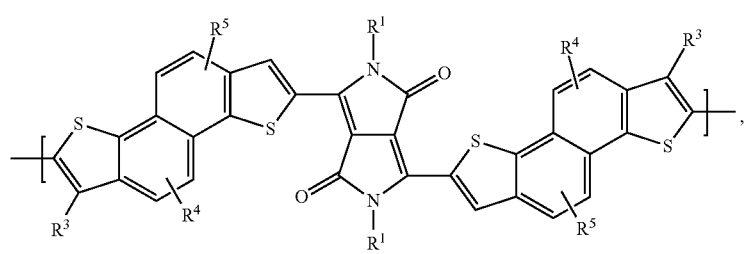
(Is)
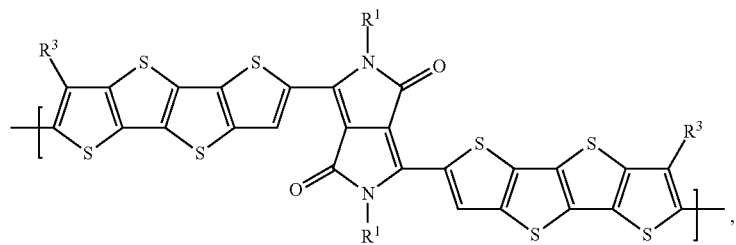
(It)
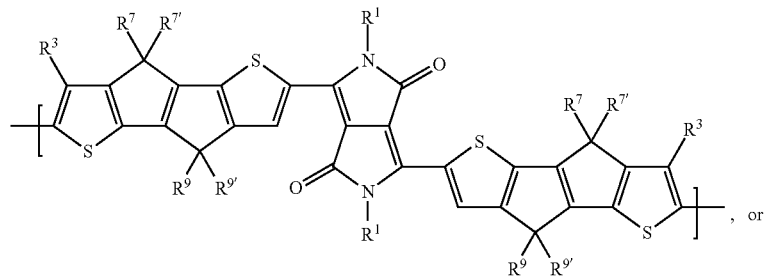
(Iu)
, or
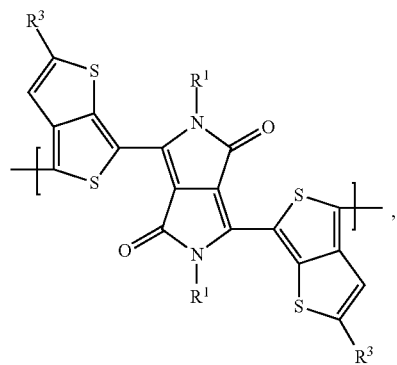
(Iv)
, $R^1$ is a $C_8$-$C_{36}$alkyl group, $R^3$ is hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;

$R^4$, $R^{4'}$, $R^5$, $R^{5'}$ and $R^6$ are independently of each other hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;

$R^7$, $R^{7'}$, $R^9$ and $R^{9'}$ are independently of each other hydrogen, $C_1$-$C_{25}$alkyl, especially $C_4$-$C_{25}$alkyl, which may optionally be interrupted by one, or more oxygen, or sulphur atoms; or $C_7$-$C_{25}$aralkyl, $R^8$ is $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_4$-$C_{25}$alkyl, which may optionally be interrupted by one or more oxygen or sulphur atoms, and $R^{12}$ and $R^{12'}$ are independently of each other hydrogen, halogen, $C_1$-$C_{25}$alkyl, especially $C_4$-$C_{25}$alkyl, which may optionally be interrupted by one, or more oxygen, or sulphur atoms, $C_1$-$C_{25}$alkoxy, or

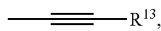

wherein $R^{13}$ is a $C_1$-$C_{10}$alkyl group, or a tri($C_1$-$C_8$alkyl)silyl group.

Most preferred $R^1$ is $C_8$-$C_{36}$alkyl, $R^3$ is hydrogen or $C_1$-$C_{25}$alkyl;

$R^4$, $R^{4'}$, $R^5$, $R^{5'}$ and $R^6$ are independently of each other hydrogen or $C_1$-$C_{25}$alkyl;

$R^7$, $R^{7'}$, $R^9$ and $R^{9'}$ are independently of each other hydrogen or $C_1$-$C_{25}$alkyl;

$R^8$ is $C_1$-$C_{25}$alkyl, especially $C_4$-$C_{25}$alkyl, and $R^{12}$ and $R^{12'}$ are independently of each other hydrogen, halogen, $C_1$-$C_{25}$alkyl, especially $C_4$-$C_{25}$alkyl, which may optionally be interrupted by one, or more oxygen, or sulphur atoms, $C_1$-$C_{25}$alkoxy, or

wherein $R^{13}$ is a $C_1$-$C_{10}$alkyl group, or a tri($C_1$-$C_8$alkyl)silyl group.

In said embodiment of the present invention compounds of the formulas Ia, Ic, Id, If, Ih, Ik, Il, In, Io, Iq, Ir, It, or Iu are most preferred, wherein $R^1$ is $C_8$-$C_{36}$alkyl, $R^3$ is hydrogen, halogen or $C_1$-$C_{25}$alkyl;

$R^4$, $R^{4'}$, $R^5$, $R^{5'}$ and $R^6$ are independently of each other hydrogen, halogen, or $C_1$-$C_{25}$alkyl;

$R^7$, $R^{7'}$, $R^9$ and $R^{9'}$ are independently of each other hydrogen, or $C_1$-$C_{25}$alkyl;

$R^8$ is $C_1$-$C_{25}$alkyl, especially $C_4$-$C_{25}$alkyl, and $R^{12}$ and $R^{12'}$ are independently of each other hydrogen, halogen, $C_1$-$C_{25}$alkyl, especially $C_4$-$C_{25}$alkyl, which may optionally be interrupted by one, or more oxygen, or sulphur atoms, $C_1$-$C_{25}$alkoxy, or

wherein $R^{13}$ is a $C_1$-$C_{10}$alkyl group, or a tri($C_1$-$C_8$alkyl)silyl group.

In a preferred embodiment of the present invention the polymer is a homopolymer of formula

wherein A is as defined above; n is number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150.

In said embodiment A is preferably a repeating unit of formula (Ia), (Ib), (Ic), (Id), (Ie), (If), (Ig), (Ih), (Ii), (Ij), (Ik), (Il), (Im), (In), (Io), (Ip), (Iq), (Ir), (Is), (It), or (Iu) as defined above.

In a further preferred embodiment of the present invention the polymer comprises one or more (repeating) unit(s) of the formula

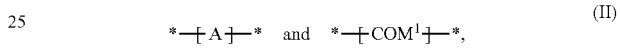

(II)

wherein A is a repeating unit of formula (I), and —COM$^1$- is a repeating unit, which is selected from a group of formula Ar$^1$, such as, for example,

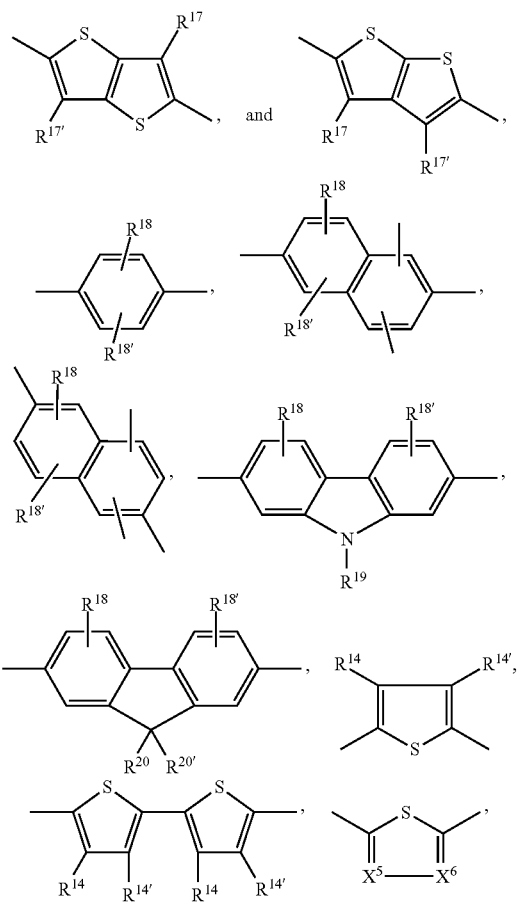

-continued

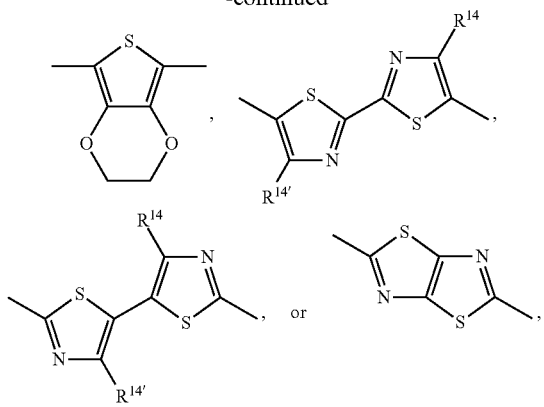

wherein
one of $X^5$ and $X^6$ is N and the other is $CR^{14}$,
$R^{14}$, $R^{14'}$, $R^{17}$ and $R^{17'}$ are independently of each other hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;
$R^{18}$ and $R^{18'}$ independently of each other hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;
$R^{19}$ is hydrogen, $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_4$-$C_{25}$alkyl, which may optionally be interrupted by one or more oxygen or sulphur atoms;
$R^{20}$ and $R^{20'}$ are independently of each other hydrogen, $C_7$-$C_{25}$aralkyl, $C_1$-$C_{25}$alkyl, especially $C_4$-$C_{25}$alkyl, which may optionally be interrupted by one, or more oxygen, or sulphur atoms,
and $Ar^1$ is as above.

$R^{14}$, $R^{14'}$, $R^{17}$ and $R^{17'}$ are preferably independently of each other hydrogen or $C_1$-$C_{25}$alkyl; $R^{18}$ and $R^{18'}$ independently of each other hydrogen, or $C_1$-$C_{25}$alkyl;
$R^{19}$ is $C_1$-$C_{25}$alkyl;
$R^{20}$ and $R^{20'}$ are independently of each other hydrogen or $C_1$-$C_{25}$alkyl,
and $Ar^1$ is as defined above.

In a preferred embodiment of the present invention the polymer is a copolymer, comprising repeating units of formula

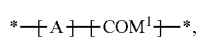 (VII)

especially a copolymer of formula

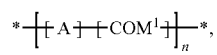

wherein A and $COM^1$ are as defined above; n is number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150.

In said embodiment A is preferably a repeating unit of formula (Ia), (Ib), (Ic), (Id), (Ie), (If), (Ig), (Ih), (Ii), (Ij), (Ik), (Il), (Im), (In), (Io), (Ip), (Iq), (Ir), (Is), (It), or (Iu) as defined above.

In said embodiment polymers are preferred, comprising one or more (repeating) unit(s) of the formula

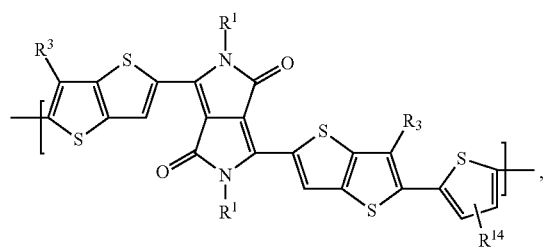 (IIa)

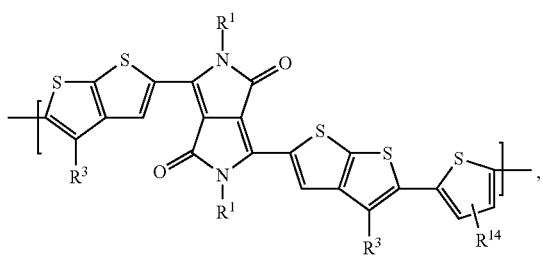 (IIb)

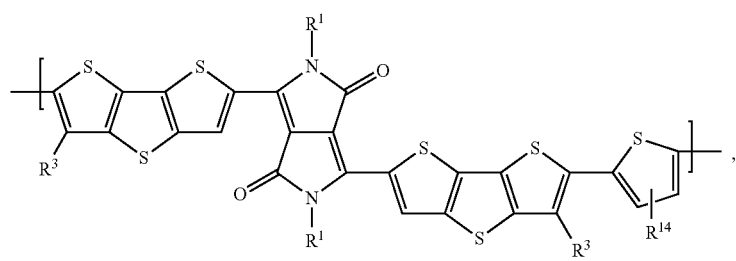 (IIc)

-continued
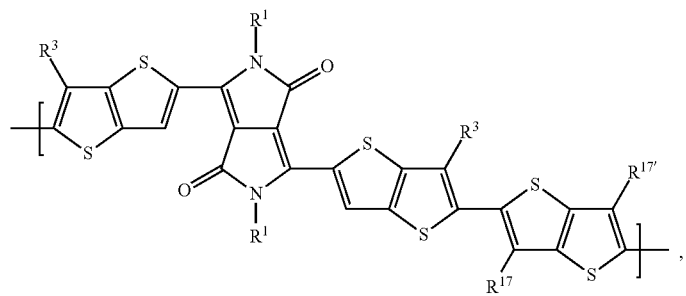
(IId)
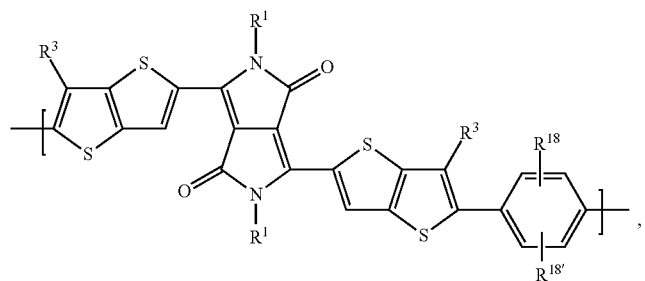
(IIe)
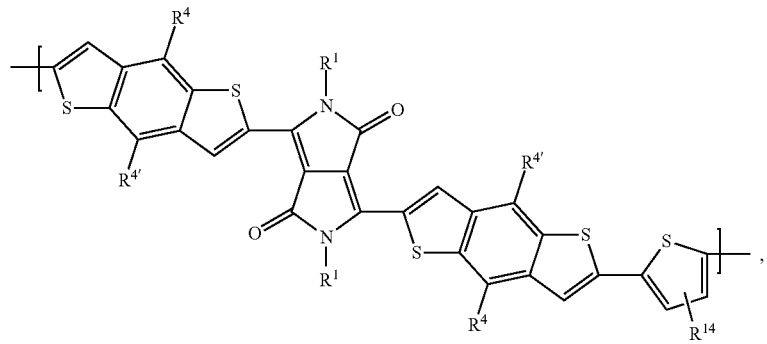
(IIf)
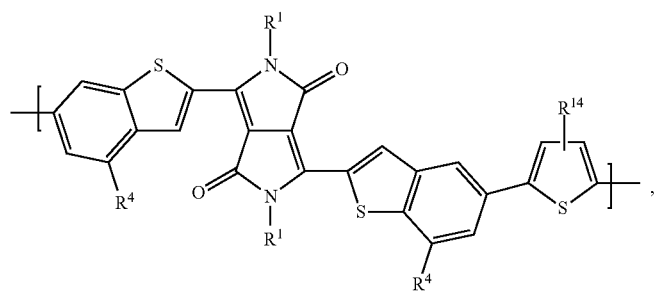
(IIg)
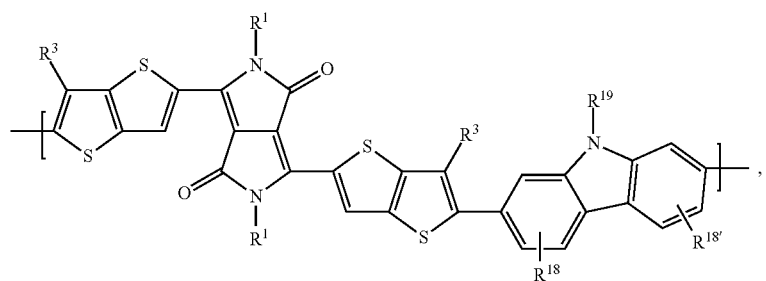
(IIh)

-continued
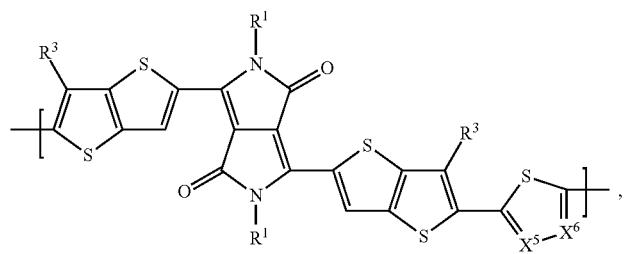
(IIi)
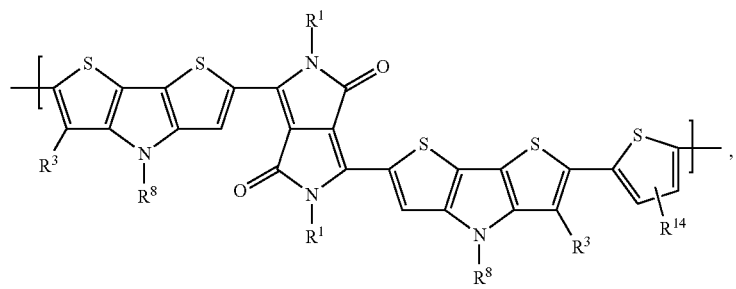
(IIj)
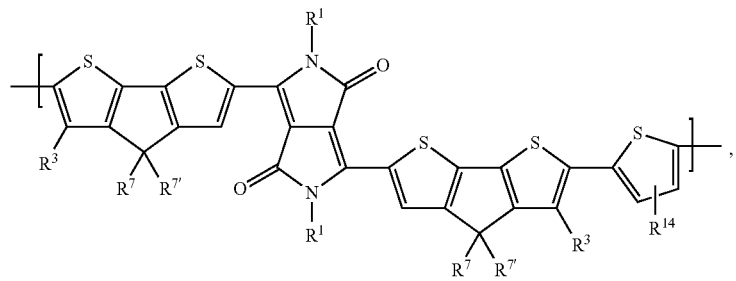
(IIk)
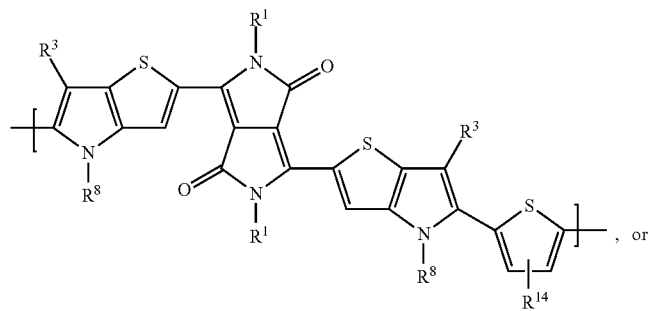
(IIl)
, or
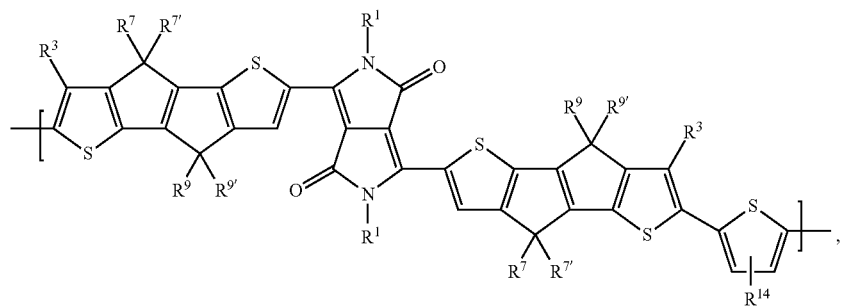
(IIm)
, $R^1$ is a $C_8$-$C_{38}$alkyl group,
$R^3$ is hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;
$R^4$, $R^{4'}$ and $R^5$ are independently of each other hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy;
$R^7$, $R^{7'}$, $R^9$ and $R^{9'}$ are independently of each other hydrogen, $C_1$-$C_{25}$alkyl, especially $C_4$-$C_{25}$alkyl, which may optionally be interrupted by one, or more oxygen, or sulphur atoms; or
$C_7$-$C_{25}$aralkyl,
$R^8$ is $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_4$-$C_{25}$alkyl, which may optionally be interrupted by one or more oxygen or sulphur atoms;
$R^{19}$ is $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_4$-$C_{25}$alkyl, which may optionally be interrupted by one or more oxygen or sulphur atoms,
one of $X^5$ and $X^6$ is N and the other is $CR^{14}$,
$R^{14}$, $R^{14'}$, $R^{17}$ and $R^{17'}$ are independently of each other hydrogen, halogen, $C_1$-$C_{25}$alkyl, especially $C_4$-$C_{25}$alkyl, which may optionally be interrupted by one or more oxygen or sulphur atoms; $C_7$-$C_{25}$aralkyl, or $C_1$-$C_{25}$alkoxy,
$R^{18}$ and $R^{18'}$ independently of each other hydrogen, halogen, $C_1$-$C_{25}$alkyl, especially $C_4$-$C_{25}$alkyl, which may optionally be interrupted by one or more oxygen or sulphur atoms, $C_7$-$C_{25}$aralkyl, or $C_1$-$C_{25}$alkoxy.

Compounds are more preferred, wherein
$R^3$ is hydrogen, halogen, $C_7$-$C_{25}$aralkyl, or $C_1$-$C_{25}$alkyl;
$R^4$, $R^{4'}$ and $R^5$ are independently of each other hydrogen, halogen, $C_7$-$C_{25}$aralkyl, or $C_1$-$C_{25}$alkyl;
$R^7$, $R^{7'}$, $R^9$ and $R^{9'}$ are independently of each other hydrogen, $C_7$-$C_{25}$aralkyl, or $C_1$-$C_{25}$alkyl;
$R^8$ is $C_1$-$C_{25}$alkyl, or $C_7$-$C_{25}$aralkyl; $R^{19}$ is $C_1$-$C_{25}$alkyl, or $C_7$-$C_{25}$aralkyl;
$R^{14}$, $R^{14'}$, $R^{17}$ and $R^{17'}$ are independently of each other hydrogen, halogen, $C_7$-$C_{25}$aralkyl, or $C_1$-$C_{25}$alkyl;
$R^{18}$ and $R^{18'}$ independently of each other hydrogen, halogen, $C_7$-$C_{25}$aralkyl, or $C_1$-$C_{25}$alkyl.

Compounds are most preferred, wherein
$R^3$ is hydrogen or $C_1$-$C_{25}$alkyl;
$R^4$, $R^{4'}$ and $R^5$ are independently of each other hydrogen, or $C_1$-$C_{25}$alkyl;
$R^7$, $R^{7'}$, $R^9$ and $R^{9'}$ are independently of each other hydrogen, or $C_1$-$C_{25}$alkyl;
$R^8$ is $C_1$-$C_{25}$alkyl; $R^{19}$ is $C_1$-$C_{25}$alkyl;
$R^{14}$, $R^{14'}$, $R^{17}$ and $R^{17'}$ are independently of each other hydrogen, or $C_1$-$C_{25}$alkyl;
$R^{18}$ and $R^{18'}$ independently of each other hydrogen, or $C_1$-$C_{25}$alkyl.

—$COM^1$- is preferably a repeating unit, which is selected from the group of formula Groups of formula are more preferred, a group of formula is most preferred.

The polymers of the present invention can comprise more than 2 different repeating units, such as, for example, repeating units A, B and D, which are different from each other. If the polymers comprise repeating units of the formula —[A—D]— and —[B—D]—, they are preferably (random) copolymers of formula

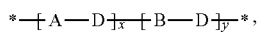

wherein x=0.995 to 0.005, y=0.005 to 0.995, especially x=0.2 to 0.8, y=0.8 to 0.2, and wherein x+y=1. A is a repeating unit of formula (I), B is a repeating unit —COM$^1$- and D is a repeating unit —COM$^1$-, with the proviso that A, B and D are different from each other.

Copolymers of formula II can be obtained, for example, by the Suzuki reaction. The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2',6'-di-alkoxybiphenyl/palladium(II) acetates, tri-alykl-phosphonium salts/palladium (0) derivatives and tri-alkylphosphine/palladium (0) derivatives. Especially preferred catalysts are 2-dicyclohexylphosphino-2',6'-di-methoxyblphenyl (sPhos)/palladium(II)acetate and, tri-tert-butylphosphonium tetrafluoroborate ((t-Bu)$_3$P*HBF$_4$/tris(dibenzylideneacetone) dipalladium (0) (Pd$_2$(dba)$_3$) and tri-tert-butylphosphine (t-Bu)$_3$P/tris(dibenzylideneacetone) dipalladium (0) (Pd$_2$(dba)$_3$). This reaction can be applied to preparing high molecular weight polymers and copolymers.

To prepare polymers corresponding to formula II a dihalogenide of formula X$^{10}$-A-X$^{10}$ is reacted with an equimolar amount of a diboronic acid or diboronate corresponding to formula

or a dihalogenide of formula

is reacted with an equimolar amount of a diboronic acid or diboronate corresponding to formula X$^{11}$-A-X$^{11}$, wherein X$^{10}$ is halogen, especially Br, and X$^{11}$ is independently in each occurrence —B(OH)$_2$, —B(OY$^1$)$_2$,

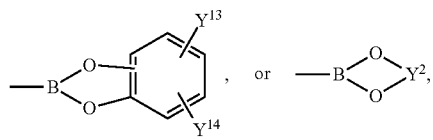

wherein Y$^1$ is independently in each occurrence a C$_1$-C$_{10}$alkyl group and Y$^2$ is independently in each occurrence a C$_2$-C$_{10}$alkylene group, such as —CY$^3$Y$^4$—CY$^5$Y$^6$—, or —CY$^7$Y$^8$—CY$^9$Y$^{10}$— CY$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a C$_1$-C$_{10}$alkyl group, especially —C(CH$_3$)$_2$C(CH$_3$)$_2$—, —C(CH$_3$)$_2$CH$_2$C(CH$_3$)$_2$—, or —CH$_2$C(CH$_3$)$_2$CH$_2$—, and Y$^{13}$ and Y$^{14}$ are independently of each other hydrogen, or a C$_1$-C$_{10}$alkyl group, in a solvent and in the presence of a catalyst. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonlum hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252. Control of molecular weight is possible by using either an excess of dibromide, diboronic acid, or diboronate, or a chain terminator.

If desired, a monofunctional halide, boronate, such as, for example, a monofunctional aryl halide, or aryl boronate, may be used as a chain-terminator in such reactions, which will result in the formation of a terminal aryl group:

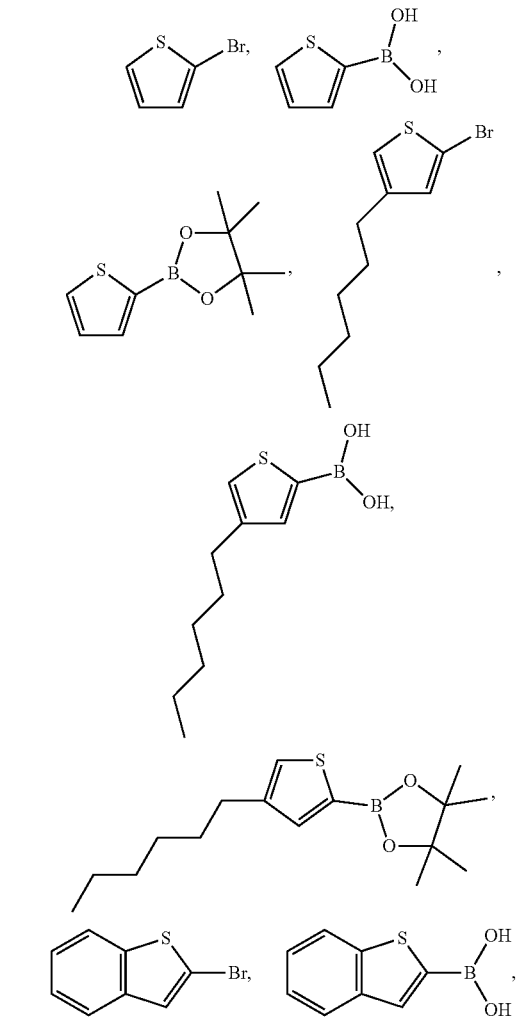

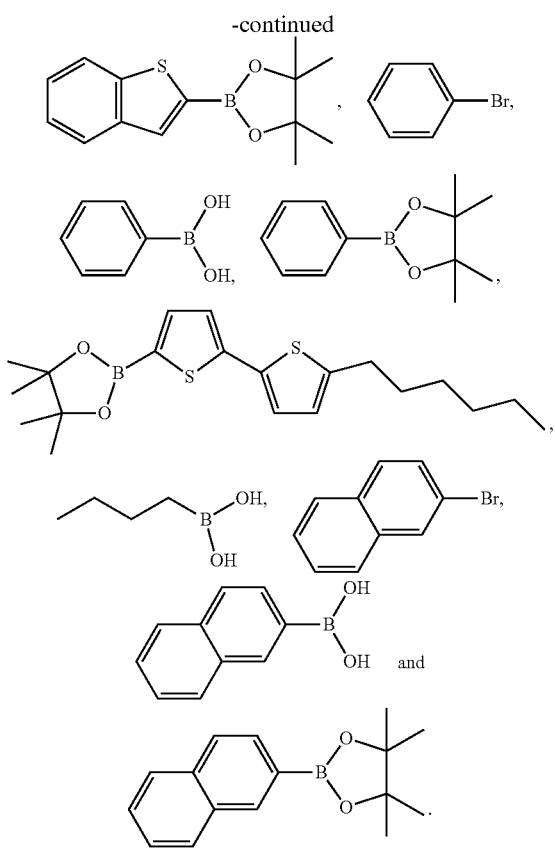

It is possible to control the sequencing of the monomeric units in the resulting copolymer by controlling the order and composition of monomer feeds in the Suzuki reaction.

The polymers of the present invention can also be sythesized by the Stille coupling (see, for example, Babudri et al, J. Mater. Chem., 2004, 14, 11-34; J. K. Stille, Angew. Chemie Int. Ed. Engl. 1986, 25, 508). To prepare polymers corresponding to formula II a dihalogenide of formula $X^{10}$-A-$X^{10}$ is reacted with an equimolar amount of an organo tin compound corresponding to formula

or a dihalogenide of formula

is reacted with an equimolar amount of an organo tin compound corresponding to formula $X^{11'}$-A-$X^{11'}$, wherein $X^{11}$ is independently in each occurrence —$SnR^{207}R^{208}R^{209}$, wherein $R^{207}$, $R^{208}$ and $R^{209}$ are identical or different and are H or $C_1$-$C_6$alkyl, or two of the groups $R^{207}$, $R^{208}$ and $R^{209}$ form a ring and these groups are optionally branched, in an inert solvent at a temperature in range from 0° C. to 200° C. in the presence of a palladium-containing catalyst. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tert-butanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

Alternatively, the polymers of the present invention can also be synthesized by the Negishi reaction using zinc reagents A-$(ZnX^{22})_2$, wherein $X^{22}$ is halogen and halides, and $COM^1$-$(X^{23})_2$, wherein $X^{23}$ is halogen or triflate, or using A-$(X^{23})_2$ and D-$(ZnX^{22})_2$. Reference is, for example, made to E. Negishi et al., Heterocycles 18 (1982) 117-22.

Alternatively, the polymers of the present invention can also be synthesized by the Hiyama reaction using organosilicon reagents A-$(SiR^{210}R^{211}R^{212})_2$, wherein $R^{210}$, $R^{211}$ and $R^{212}$ are identical or different and are halogen, $C_1$-$C_6$alkyl and $COM^1$-$(X^{23})_2$, wherein $X^{23}$ is halogen or triflate, or using A-$(X^{23})_2$ and $COM^1$-$(SiR^{210}R^{211}R^{212})_2$. Reference is, for example, made to T. Hiyama et al., Pure Appl. Chem. 66 (1994) 1471-1478 and T. Hiyama et al., Synlett (1991) 845-853.

Homopolymers of the type $(A)_n$ can be obtained via Yamamoto coupling of dihalides $X^{10}$-A-$X^{10}$, where $X^{10}$ is halogen, preferably bromide. Alternatively homopolymers of the type (A), can be obtained via oxidative polymerization of units $X^{10}$-A-$X^{10}$, where $X^{10}$ is hydrogen, e.g. with $FeCl_3$ as oxidizing agent.

The polymers, wherein $R^1$ and/or $R^2$ are hydrogen can be obtained by using a protecting group which can be removed after polymerization (see, for example, EP-A-0 648 770, EP-A-0 648 817, EP-A-0 742 255, EP-A-0 761 772, WO98/32802, WO98/45757, WO98/58027, WO99/01511, WO00/17275, WO00/39221, WO00/63297 and EP-A-1 086 984). Conversion of the pigment precursor into its pigmentary form is carried out by means of fragmentation under known conditions, for example thermally, optionally in the presence of an additional catalyst, for example the catalysts described in WO00/36210.

An example of such a protecting group is group of formula

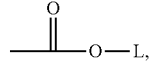

wherein L is any desired group suitable for imparting solubility.

L is preferably a group of formula

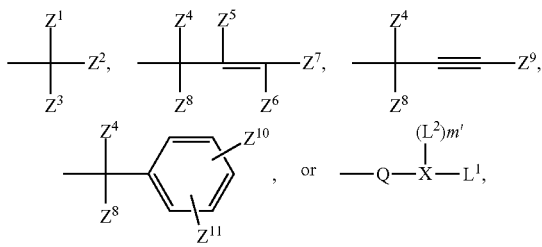

wherein $Z^1$, $Z^2$ and $Z^3$ are independently of each other $C_1$-$C_6$alkyl,
$Z^4$ and $Z^8$ are independently of each other $C_1$-$C_6$alkyl, $C_1$-$C_6$alkyl interrupted by oxygen, sulfur or $N(Z^{12})_2$, or unsubstituted or $C_1$-$C_6$alkyl-, $C_1$-$C_6$alkoxy-, halo-, cyano- or nitro-substituted phenyl or biphenyl,
$Z^5$, $Z^6$ and $Z^7$ are independently of each other hydrogen or $C_1$-$C_6$alkyl,
$Z^9$ is hydrogen, $C_1$-$C_6$alkyl or a group of formula

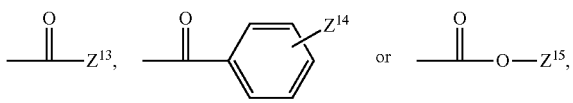

$Z^{10}$ and $Z^{11}$ are each independently of the other hydrogen, $C_1$-$C_6$alkyl, $C_1$-$C_6$alkoxy, halogen, cyano, nitro, $N(Z^{12})_2$, or unsubstituted or halo-, cyano-, nitro-, $C_1$-$C_6$alkyl- or $C_1$-$C_6$alkoxy-substituted phenyl,
$Z^{12}$ and $Z^{13}$ are $C_1$-$C_6$alkyl, $Z^{14}$ is hydrogen or $C_1$-$C_6$alkyl, and $Z^{15}$ is hydrogen, $C_1$-$C_6$alkyl, or unsubstituted or $C_1$-$C_6$alkyl-substituted phenyl,
Q is p,q-$C_2$-$C_6$alkylene unsubstituted or mono- or poly-substituted by $C_1$-$C_6$alkoxy, $C_1$-$C_6$alkylthio or $C_2$-$C_{12}$dialkylamino, wherein p and q are different position numbers,
X is a hetero atom selected from the group consisting of nitrogen, oxygen and sulfur, m' being the number 0 when X is oxygen or sulfur and m being the number 1 when X is nitrogen, and
$L^1$ and $L^2$ are independently of each other unsubstituted or mono- or poly-$C_1$-$C_{12}$alkoxy-, —$C_1$-$C_{12}$alkylthio-, —$C_2$-$C_{24}$dialkylamino-, —$C_6$-$C_{12}$aryloxy-, —$C_6$-$C_{12}$arylthio-, —$C_7$-$C_{24}$alkylarylamino- or —$C_{12}$-$C_{24}$diarylamino-substituted $C_1$-$C_6$alkyl or [-(p',q'—$C_2$-$C_6$alkylene)-Z—]$_{n'}$—$C_1$-$C_6$alkyl, n' being a number from 1 to 1000, p' and q' being different position numbers, each Z independently of any others being a hetero atom oxygen, sulfur or $C_1$-$C_{12}$alkyl-substituted nitrogen, and it being possible for $C_2$-$C_6$alkylene in the repeating [—$C_2$-$C_6$alkylene-Z-] units to be the same or different,
and $L_1$ and $L_2$ may be saturated or unsaturated from one to ten times, may be uninterrupted or interrupted at any location by from 1 to 10 groups selected from the group consisting of —(C=O)— and —$C_6H_4$—, and may carry no further substituents or from 1 to 10 further substituents selected from the group consisting of halogen, cyano and nitro. Most preferred L is a group of formula

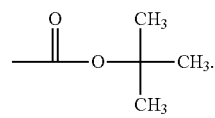

The synthesis of the compounds of formula Br-A-Br is described in WO08/000664, and WO09/047104, or can be done in analogy to the methods described therein. The synthesis of N-aryl substituted compounds of formula Br-A-Br can be done in analogy to the methods described in U.S. Pat. No. 5,354,869 and WO03/022848.
Compounds of the formula

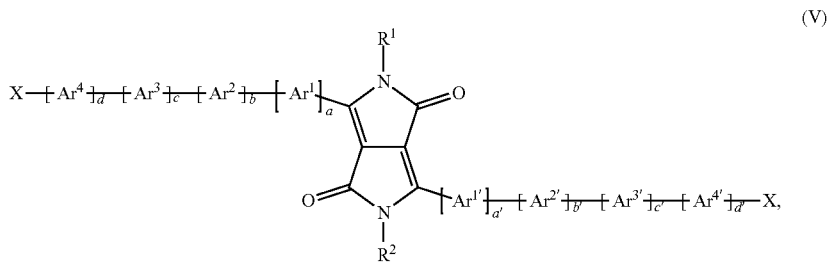

wherein a, a', b, b', c, c', d, d', $R^1$, $R^2$, $Ar^1$, $Ar^{1'}$, $A^2$, $A^{2'}$, $Ar^3$, $Ar^{3'}$, $Ar^4$ and $Ar^{4'}$ are as defined in claim 1, and X is $ZnX^{12}$, —$SnR^{207}R^{208}R^{209}$, wherein $R^{207}$, $R^{208}$ and $R^{209}$ are identical or different and are H or $C_1$-$C_6$alkyl, wherein two radicals optionally form a common ring and these radicals are optionally branched or unbranched and $X^{12}$ is a halogen atom, very especially I, or Br; or —$OS(O)_2CF_3$, —$OS(O)_2$-aryl, especially

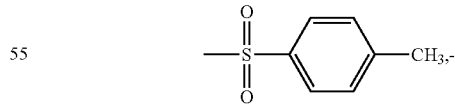

$OS(O)_2CH_3$, —$B(OH)_2$, —$B(OY^1)_2$,

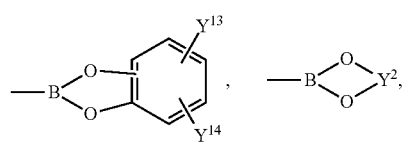

—$BF_4Na$, or —$BF_4K$, wherein $Y^1$ is independently in each occurrence a $C_1$-$C_{10}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, especially —$C(CH_3)_2C(CH_3)_2$—, —$C(CH_3)_2CH_2C(CH_3)_2$—,
or —$CH_2C(CH_3)_2CH_2$—, and $Y^{13}$ and $Y^{14}$ are independently of each other hydrogen, or a $C_1$-$C_{10}$alkyl group; are new and form a further subject of the present invention.

A mixture containing a polymer of the present invention results in a semi-conducting layer comprising a polymer of the present invention (typically 5% to 99.9999% by weight, especially 20 to 85% by weight) and at least another material. The other material can be, but is not restricted to a fraction of the same polymer of the present invention with different molecular weight, another polymer of the present invention, a semi-conducting polymer, organic small molecules, such as, for example, a compound of formula III, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

Accordingly, the present invention also relates to an organic semiconductor material, layer or component, comprising a polymer according to the present invention.

The polymers of the invention according to the present invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

There are numerous types of semiconductor devices. Common to all is the presence of one or more semiconductor materials. Semiconductor devices have been described, for example, by S. M. Sze in Physics of Semiconductor Devices, $2^{nd}$ edition, John Wiley and Sons, New York (1981). Such devices include rectifiers, transistors (of which there are many types, including p-n-p, n-p-n, and thin-film transistors), light emitting semiconductor devices (for example, organic light emitting diodes in display applications or backlight in e.g. liquid crystal displays), photoconductors, current limiters, solar cells, thermistors, p-n junctions, field-effect diodes, Schottky diodes, and so forth. In each semiconductor device, the semiconductor material is combined with one or more metals, metal oxides, such as, for example, indium tin oxide (ITO), and/or insulators to form the device. Semiconductor devices can be prepared or manufactured by known methods such as, for example, those described by Peter Van Zant in Microchip Fabrication, Fourth Edition, McGraw-Hill, New York (2000). In particular, organic electronic components can be manufactured as described by D. R. Gamota et al. In Printed Organic and Molecular Electronics, Kluver Academic Publ., Boston, 2004.

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, $2^{nd}$ edition, John Wiley and Sons, page 492, New York (1981)). These components can be assembled in a variety of configurations. More specifically, an OFET has an organic semiconductor layer.

Typically, a substrate supports the OFET during manufacturing, testing, and/or use. Optionally, the substrate can provide an electrical function for the OFET. Useful substrate materials include organic and inorganic materials. For example, the substrate can comprise silicon materials inclusive of various appropriate forms of silicon, inorganic glasses, ceramic foils, polymeric materials (for example, acrylics, polyester, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive oxides, such as indium tin oxide, or conducting inks/pastes comprised of carbon black/graphite or colloidal silver dispersions, optionally containing polymer binders can also be used. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OFETs, the same material can provide the gate electrode function and also provide the support function of the substrate. For example, doped silicon can function as the gate electrode and support the OFET.

The gate dielectric is generally provided on the gate electrode. This gate dielectric electrically insulates the gate electrode from the balance of the OFET device. Useful materials for the gate dielectric can comprise, for example, an inorganic electrically insulating material.

The gate dielectric (insulator) can be a material, such as, an oxide, nitride, or it can be a material selected from the family of ferroelectric insulators (e.g. organic materials such as poly(vinylidene fluoride/trifluoroethylene or poly(m-xylene adipamide)), or it can be an organic polymeric insulator (e.g. poly(methacrylate)s, poly(acrylate)s, polyimides, benzocyclobutenes (BCBs), parylenes, polyvinylalcohol, polyvinylphenol (PVP), polystyrenes, polyester, polycarbonates) as for example described in J. Veres et al. Chem. Mat. 2004, 16, 4543 or A. Facchetti et al. Adv. Mat. 2005, 17, 1705. Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulphide, including but not limited to $PbZr_xTi_{1-x}O_3$(PZT), $Bi_4Ti_3O_{12}$, $BaMgF_4$, $Ba(Zr_{1-x}Ti_x)O_3$ (BZT). In addition, alloys, hybrid materials (e.g. polysiloxanes or nanoparticle-filled polymers) combinations, and multilayers of these materials can be used for the gate dielectric. The thickness of the dielectric layer is, for example, from about 10 to 1000 nm, with a more specific thickness being about 100 to 500 nm, providing a capacitance in the range of 0.1-100 nanofarads (nF).

The source electrode and drain electrode are separated from the gate electrode by the gate dielectric, while the organic semiconductor layer can be over or under the source electrode and drain electrode. The source and drain electrodes can be any useful conductive material favourably providing a low resistance ohmic contact to the semiconductor layer. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or (ink jet) printing methods. The patterning of these electrodes can be accomplished by known methods such as shadow masking, additive photolithography, subtractive photolithography, printing, microcontact printing, and pattern coating.

The present invention further provides an organic field effect transistor device comprising a plurality of electrically conducting gate electrodes disposed on a substrate; a gate insulator layer disposed on said electrically conducting gate electrodes; a plurality of sets of electrically conductive source and drain electrodes disposed on said insulator layer such that each of said sets is in alignment with each of said gate electrodes; an organic semiconductor layer disposed in the channel between source and drain electrodes on said insulator layer substantially overlapping said gate electrodes; wherein said organic semiconductor layer comprises a polymer of the present invention, or an organic semiconductor material, layer or component.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a plurality of sets of electrically conductive source and drain electrodes on said layer such that each of said sets is in alignment with each of said gate electrodes;
depositing a layer of a polymer of the present invention on said insulator layer such that said layer of the polymer of the present invention, or a mixture containing a polymer of the present invention, substantially overlaps said gate electrodes; thereby producing the thin film transistor device.

Alternatively, an OFET is fabricated by, for example, by solution deposition of a polymer on a highly doped silicon substrate covered with a thermally grown oxide layer followed by vacuum deposition and patterning of source and drain electrodes.

In yet another approach, an OFET is fabricated by deposition of source and drain electrodes on a highly doped silicon substrate covered with a thermally grown oxide and then solution deposition of the polymer to form a thin film.

The gate electrode could also be a patterned metal gate electrode on a substrate or a conducting material such as, a conducting polymer, which is then coated with an insulator applied either by solution coating or by vacuum deposition on the patterned gate electrodes.

Any suitable solvent can be used to dissolve, and/or disperse the polymers of the present application, provided it is inert and can be removed partly, or completely from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated or fluorinated hydrocarbons, esters, ethers, amides, such as chloroform, tetrachloroethane, tetrahydrofuran, toluene, tetraline, decaline, anisole, xylene, ethyl acetate, methyl ethyl ketone, dimethyl formamide, chloroform, chlorobenzene, dichlorobenzene, trichlorobenzene, propylene glycol monomethyl ether acetate (PGMEA) and mixtures thereof. Preferred solvents are xylene, toluene, tetraline, decaline, chlorinated ones such as chloroform, chlorobenzene, ortho-dichlorobenzene, trichlorobenzene and mixtures thereof. The solution, and/or dispersion is then applied by a method, such as, spin-coating, dip-coating, screen printing, microcontact printing, doctor blading or other solution application techniques known in the art on the substrate to obtain thin films of the semiconducting material.

The term "dispersion" covers any composition comprising the semiconductor material of the present invention, which is not fully dissolved in a solvent. The dispersion can be done selecting a composition including at least a polymer of the present invention, or a mixture containing a polymer of the present invention, and a solvent, wherein the polymer exhibits lower solubility in the solvent at room temperature but exhibits greater solubility in the solvent at an elevated temperature, wherein the composition gels when the elevated temperature is lowered to a first lower temperature without agitation;
dissolving at the elevated temperature at least a portion of the polymer in the solvent; lowering the temperature of the composition from the elevated temperature to the first lower temperature; agitating the composition to disrupt any gelling, wherein the agitating commences at any time prior to, simultaneous with, or subsequent to the lowering the elevated temperature of the composition to the first lower temperature; depositing a layer of the composition wherein the composition is at a second lower temperature lower than the elevated temperature; and drying at least partially the layer.

The dispersion can also be constituted of (a) a continuous phase comprising a solvent, a binder resin, and optionally a dispersing agent, and (b) a disperse phase comprising a polymer of the present invention, or a mixture containing a polymer of the present invention. The degree of solubility of the polymer of the present invention in the solvent may vary for example from 0% to about 20% solubility, particularly from 0% to about 5% solubility.

Preferably, the thickness of the organic semiconductor layer is in the range of from about 5 to about 1000 nm, especially the thickness is in the range of from about 10 to about 100 nm.

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, Ink Jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photo-diodes, or security devices and the like. Due to its ambipolarity the material can also be used in Organic Light Emitting Transistors (OLET).

A further aspect of the present invention is an organic semiconductor material, layer or component comprising one or more polymers of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The polymers of the present invention are typically used as organic semiconductors in form of thin organic layers or films, preferably less than 30 microns thick. Typically the semiconducting layer of the present invention is at most 1 micron (=1 μm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
a source electrode,
a drain electrode,
a gate electrode,
a semiconducting layer,
one or more gate insulator layers, and
optionally a substrate, wherein the semiconductor layer comprises one or more polymers of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a polymer of the present invention located on the second side of the insulator, and a drain electrode and a source electrode located on the polymer layer.

The OFET device can be a top gate device or a bottom gate device.

Suitable structures and manufacturing methods of an OFET device are known to the skilled in the art and are described in the literature, for example in WO03/052841.

The gate insulator layer may comprise for example a fluoropolymer, like e.g. the commercially available Cytop 809M®, or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43® (Acros, No. 12377).

The semiconducting layer comprising a polymer of the present invention may additionally comprise at least another material. The other material can be, but is not restricted to another polymer of the present invention, a semi-conducting polymer, a polymeric binder, organic small molecules different from a polymer of the present invention, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more polymers of the present invention and a polymeric binder. The ratio of the polymers of the present invention to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The polymers of the present invention are advantageously used in organic photovoltaic (PV) devices (solar cells). Accordingly, the invention provides PV devices comprising a polymer according to the present invention. A device of this construction will also have rectifying properties so may also be termed a photodiode. Photoresponsive devices have application as solar cells which generate electricity from light and as photodetectors which measure or detect light.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor. For heterojunction solar cells the active layer comprises preferably a mixture of a polymer of the present invention and a fullerene, such as [60]PCBM (=6,6-phenyl-$C_{61}$-butyric acid methyl ester), or [70]PCBM, in a weight ratio of 1:1 to 1:3.

The structure and the components of the photovoltaic device are described in more detail below.

In a further embodiment the present invention relates to compounds of the formula

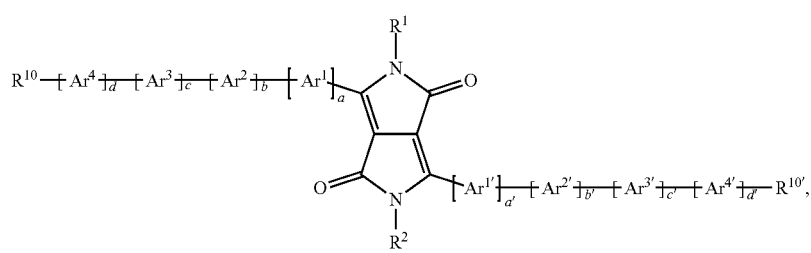
(III)

wherein a, a', b, b', c, c', d, d', $R^1$, $R^2$, $Ar^1$, $Ar^{1'}$, $Ar^2$, $Ar^{2'}$, $Ar^3$, $Ar^{3'}$, $A^4$ and $Ar^{4'}$ are as defined above, $R^{10}$ and $R^{10'}$ are independently of each other hydrogen, halogen, $C_1$-$C_{25}$alkyl, $C_1$-$C_{25}$alkoxy, or a group of one of the formulae IVa to IVi,

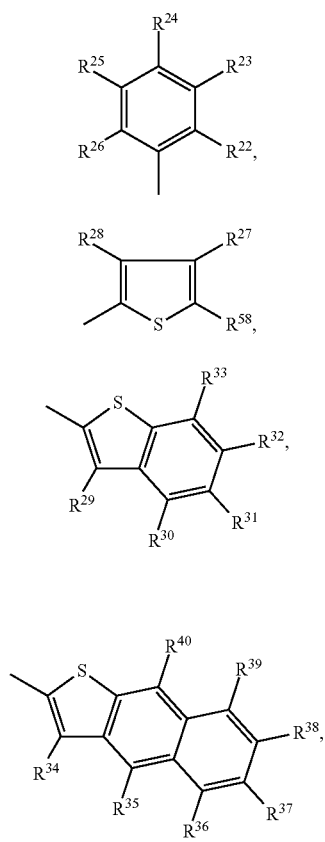

(IVa)

(IVb)

(IVc)

(IVd)

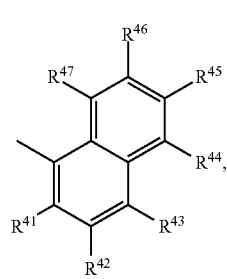

(IVe)

-continued

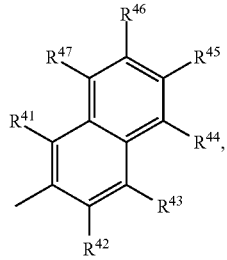

(IVf)

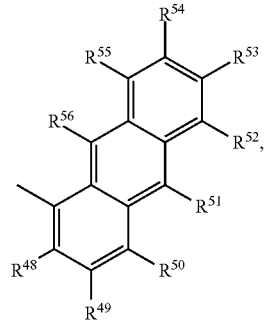

(IVg)

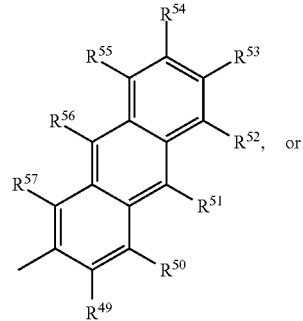

(IVh)

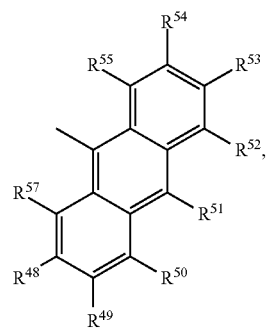

(IVi)

wherein $R^{22}$ to $R^{26}$ and $R^{29}$ to $R^{58}$ represent independently of each other H, halogen, $C_1$-$C_{25}$alkyl, $C_1$-$C_{25}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $C_7$-$C_{25}$aralkyl, which is substituted by G, $R^{27}$ and $R^{28}$ are independently of each other hydrogen, $C_1$-$C_{25}$alkyl, or $C_7$-$C_{25}$aralkyl, or $R^{27}$ and $R^{28}$ together represent alkylene or alkenylene which may be both bonded via oxygen and/or sulfur to the thienyl residue and which may both have up to 25 carbon atoms, D is —CO—, —COO—, —S—, —O—, or —NR$^{112}$—, E is $C_1$-$C_8$thioalkoxy, $C_1$-$C_8$alkoxy, CN, —NR$^{112}$R$^{113}$, —CONR$^{112}$R$^{113}$, or halogen, G is E, or $C_1$-$C_{18}$alkyl, and $R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—; with the proviso that the following compound

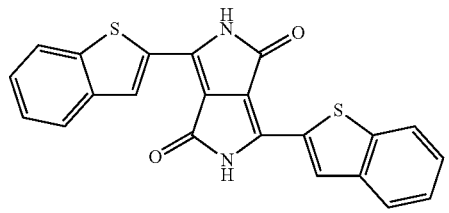 [SMILES: O=C1NC(c2cc3ccccc3s2)=C2C(=O)NC(c3cc4ccccc4s3)=C12]

is excluded.

Preferably, $R^{10}$ and $R^{10'}$ are independently of each other hydrogen, $C_1$-$C_{25}$alkyl or a group of one of the formulae IVb, or VIc, wherein $R^{22}$ to $R^{26}$ and $R^{29}$ to $R^{58}$ represent independently of each other hydrogen, or $C_1$-$C_{25}$alkyl.

In a preferred embodiment of the present invention $Ar^1$ and $Ar^{1'}$ are selected from groups of formula Xa, Xb, Xc, Xd, and Xg, especially Xa, Xc and Xg. In another preferred embodiment of the present invention $Ar^1$ and $Ar^{1'}$ are selected from groups of formula Xe, Xf, Xh, Xi, Xj, Xk, Xm, Xn, Xq, Xr, Xv, Xx, Xy, XIa, XIb, XIg, XIh, XIi and XIl, especially Xe, Xj, Xm, Xn, Xr, Xv, Xx, XIb and XIi.

In said embodiment compounds of formula

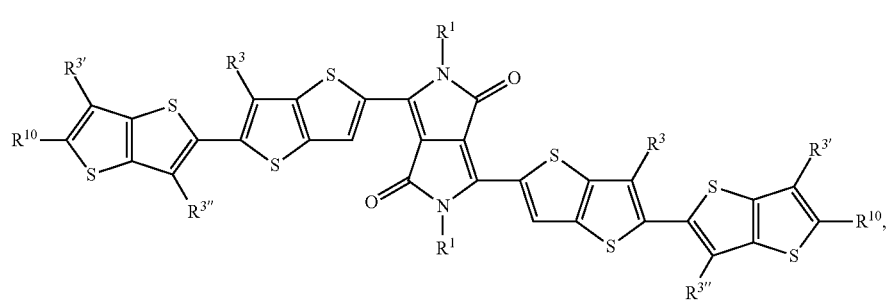

(IIIa)

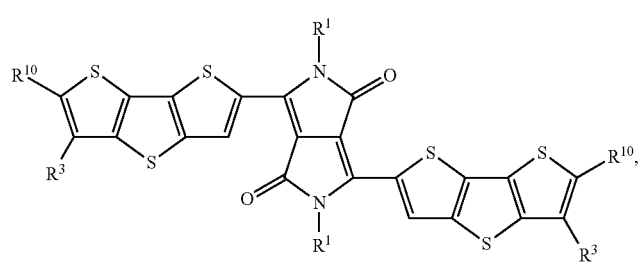

(IIIb)

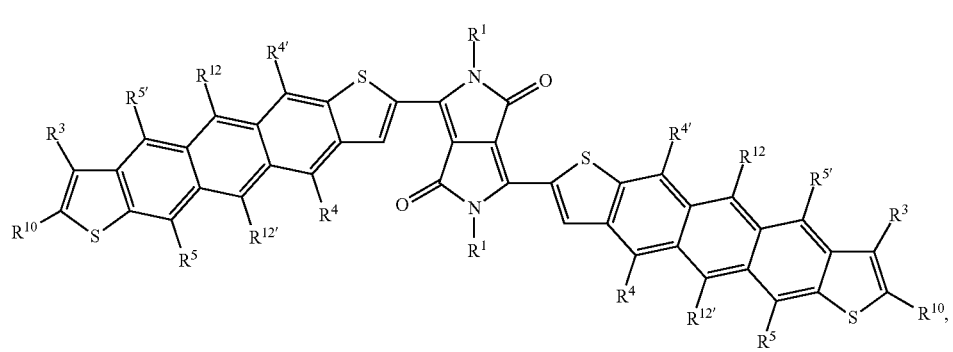

(IIIc)

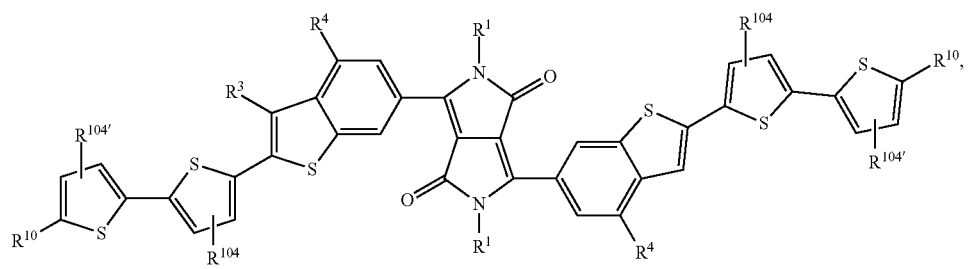
(IIId)
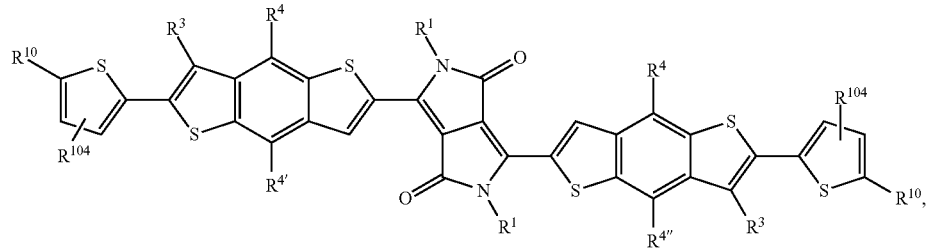
(IIIe)
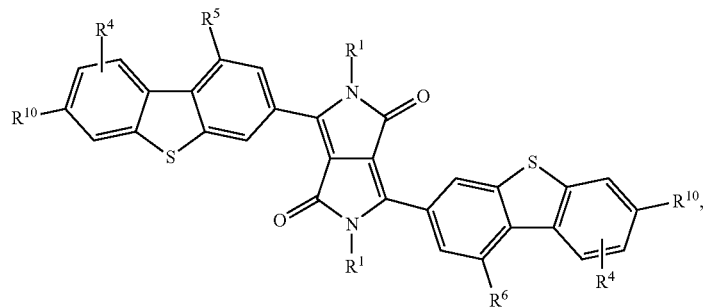
(IIIf)
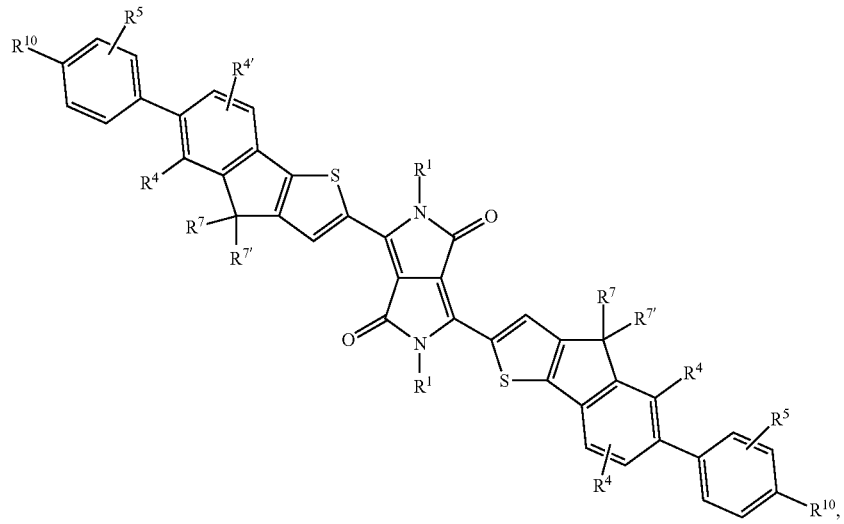
(IIIg)

-continued
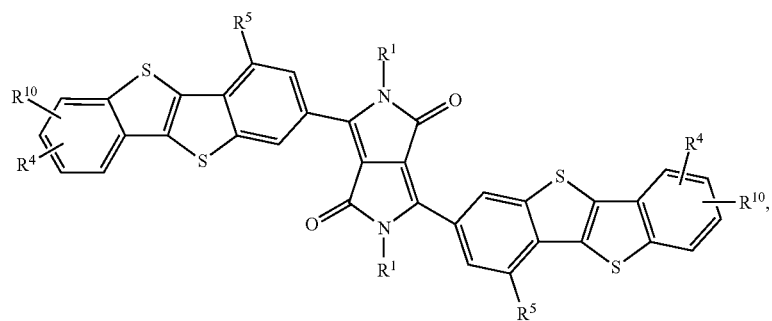
(IIIh)
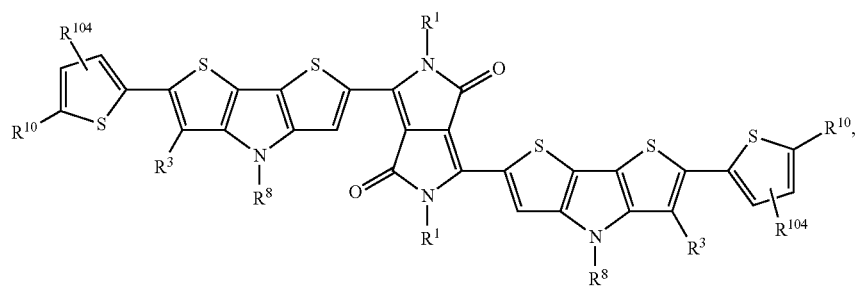
(IIIi)
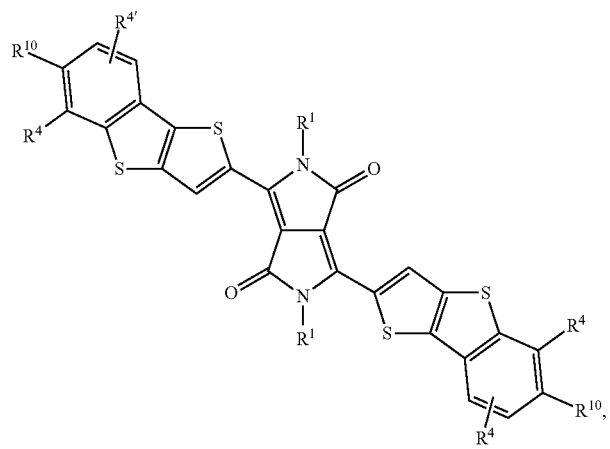
(IIIj)
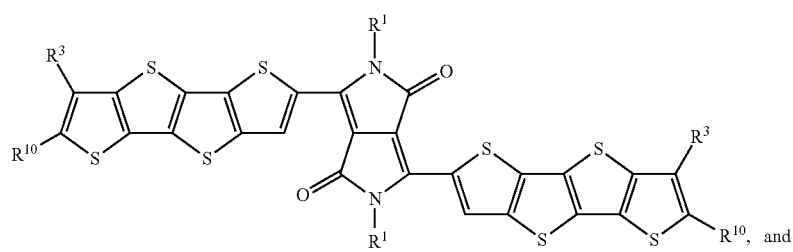
(IIIk)
and (III1)

are more preferred, wherein
$R^1$ is a $C_8$-$C_{36}$alkyl group,
$R^3$ and $R^{3'}$ are independently of each other hydrogen, halogen, $C_1$-$C_{25}$alkyl, especially $C_4$-$C_{25}$alkyl, which may optionally be interrupted by one or more oxygen or sulphur atoms, or $C_1$-$C_{25}$alkoxy; $R^{3''}$ has the meaning of $R^3$;
$R^{104}$ and $R^{104'}$ are independently of each other hydrogen, halogen, $C_1$-$C_{25}$alkyl, especially $C_4$-$C_{25}$alkyl, which may optionally be interrupted by one or more oxygen or sulphur atoms, or $C_1$-$C_{25}$alkoxy;
$R^4$, $R^{4'}$, $R^5$, and $R^{5'}$ are independently of each other hydrogen, halogen, $C_1$-$C_{25}$alkyl, especially $C_4$-$C_{25}$alkyl, which may optionally be interrupted by one or more oxygen or sulphur atoms, or $C_1$-$C_{25}$alkoxy;
$R^7$, $R^{7'}$, $R^9$ and $R^{9'}$ are independently of each other hydrogen, $C_1$-$C_{25}$alkyl, especially $C_4$-$C_{25}$alkyl, which may optionally be interrupted by one, or more oxygen, or sulphur atoms,
$R^8$ is $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, especially $C_4$-$C_{25}$alkyl, which may optionally be interrupted by one or more oxygen or sulphur atoms,
$R^{12}$ and $R^{12'}$ are independently of each other hydrogen, halogen, $C_1$-$C_{25}$alkyl, especially $C_4$-$C_{25}$alkyl, which may optionally be interrupted by one, or more oxygen, or sulphur atoms, $C_1$-$C_{25}$alkoxy, or =$R^{13}$, wherein $R^{13}$ is a $C_1$-$C_{10}$alkyl group, or a tri($C_1$-$C_8$alkyl)silyl group, and $R^{10}$ is hydrogen, $C_1$-$C_{25}$alkyl or a group of one of the formulae IVb, or VIc, wherein $R^{22}$ to $R^{26}$ and $R^{29}$ to $R^{58}$ represent independently of each other hydrogen, or $C_1$-$C_{25}$alkyl In said embodiment of the present invention compounds of the formulas IIIa, IIIb, IIIc, IIIe, IIIg, IIIi, IIIj, IIIk and IIIl are preferred, compounds of the formulas IIIa, IIIb, IIIc, IIIe, IIIj and IIIl are more preferred, and compounds of the formula IIIe are most preferred, wherein
$R^1$ is $C_8$-$C_{36}$alkyl,
$R^3$ is hydrogen, halogen or $C_1$-$C_{25}$alkyl;
$R^4$, $R^{4'}$, $R^5$, $R^{5'}$ and $R^6$ are independently of each other hydrogen, halogen, or $C_1$-$C_{25}$alkyl;
$R^7$, $R^{7'}$, $R^9$ and $R^{9'}$ are independently of each other hydrogen, or $C_1$-$C_{25}$alkyl;
$R^8$ is $C_1$-$C_{25}$alkyl, especially $C_4$-$C_{25}$alkyl.

The process for the preparation of a compound of the formula III comprises
(a) reacting (in the presence of a strong base) one mole of a disuccinate, like dimethyl succinate, with 1 mole of a nitrile of the formula $$R^{10}\!-\!(Ar^4)_d\!-\!(Ar^3)_c\!-\!(Ar^2)_b\!-\!(Ar^1)_a\!-\!C\!\equiv\!N$$

and 1 mole of a nitrile of the formula $$N\!\equiv\!C\!-\!(Ar^{1'})_{a'}\!-\!(Ar^{3'})_{b'}\!-\!(Ar^{3'})_{c'}\!-\!(Ar^{4'})_{d'}\!-\!R^{10'},$$

(b) optionally reacting a compound of formula (VI)

obtained in step a) with a compound of the formula $R^1$—Hal, wherein Hal is halogen, —O— mesylate, or —O-tosylate, preferably bromide or iodide, in the presence of a suitable base, like potassium carbonate, in a suitable solvent, like N-methyl-pyrrolidone, wherein $R^{10}$ and $R^{10'}$ are as defined above, and (c) optionally reacting a compound of formula

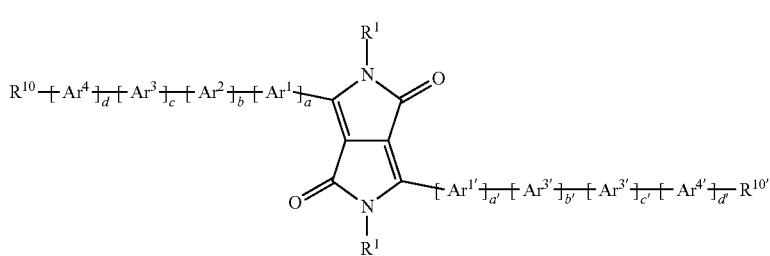

(VII)

obtained in step b), wherein $R^{10}$ and $R^{10'}$ are hydrogen, with a suitable brominating agent, like N-bromo-succinimide, wherein a, a', b, b', c, c', d, d', $R^1$, $R^2$, $Ar^1$, $Ar^{1'}$, $Ar^2$, $Ar^{2'}$, $Ar^3$, $Ar^{3'}$, $Ar^4$ and $Ar^{4'}$ are as defined above.

The compounds of the formula III can be manufactured by known methods. Reference is, for example, made to pages 16 to 20 of WO09/047104.

Compounds of the formula VI can be obtained as described in U.S. Pat. No. 4,579,949 by reacting (in the presence of a strong base) one mole of a disuccinate, like dimethyl succinate, with 1 mole of a nitrile of the formulae

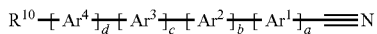

and 1 mole of a nitrile of the formula

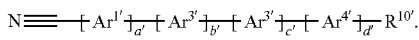

Symmetrical compounds of the formula VI are obtained by reacting (in the presence of a strong base) one mole of a disuccinate, like dimethyl succinate, with 2 mole of a nitrile of the formula

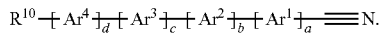

Alternatively, said compounds of formulae VI can be obtained as described in U.S. Pat. No. 4,659,775 by reacting a nitrile with a suitable ester, like a pyrrolinon-3-carboxylic ester derivative.

The compound of the formula VI is N-alkylated for introduction of the group $R^1$, e.g. by reaction with a bromide of the formula $R^1$—Br in the presence of a suitable base, like potassium carbonate, in a suitable solvent, like N-methyl-pyrrolidone. The reaction is carried out at a temperature from about room temperature to about 180° C., preferably from about 100° C. to about 170° C., e.g. at 140° C.

The thus obtained compound of the formula VII is then reacted with a suitable brominating agent, like N-bromo-succinimide, to yield a compound of the formulae VI, respectively. The bromination is carried out in a suitable solvent, like chloroform, using two equivalents of N-bromo-succinimide at a temperature between −30° C. and +50° C., preferably between −10° C. and room temperature, e.g. at 0° C.

Advantageously, the compound of formula III, or an organic semiconductor material, layer or component, comprising the compound of formula III can be used in organic photovoltaics (solar cells) and photodiodes, or in an organic field effect transistor (OFET).

A mixture containing the compound of formula III results in a semi-conducting layer comprising the compound of formula III (typically 5% to 99.9999% by weight, especially 20 to 85% by weight) and at least another material. The other material can be, but is not restricted to another compound of formula III, a polymer of the present invention, a semi-conducting polymer, a non-conductive polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

Accordingly, the present invention also relates to an organic semiconductor material, layer or component, comprising a compound of formula III and to a semiconductor device, comprising a compound of formula III and/or an organic semiconductor material, layer or component.

The semiconductor is preferably an organic photovoltaic (PV) device (solar cell), a photodiode, or an organic field effect transistor. The structure and the components of the OFET device has been described in more detail above.

Accordingly, the invention provides organic photovoltaic (PV) devices (solar cells) comprising a compound of the formula III.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula III. Preferably, the photoactive layer is made of a compound of the formula III, as an electron donor and an acceptor material, like a fullerene, particularly a functionalized fullerene PCBM, as an electron acceptor. As stated above, the photoactive layer may also contain a polymeric binder. The ratio of the small molecules of formula III to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compounds of formula III, or any semi-conducting polymer, such as, for example, a polymer of formula I, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a compound of the formula III, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyltetrahydrofurane, N,N-dimethylformamide, acetone, acetonitrile, anisole, dichloromethane, dimethyisulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the compounds of the formula III can also be used alone or together with other materials in or as alignment layers in LCD or OLED devices, as described for example in US2003/0021913.

An OFET device according to the present invention preferably comprises:
a source electrode,
a drain electrode,
a gate electrode,
a semiconducting layer,
one or more gate insulator layers, and
optionally a substrate, wherein the semiconductor layer comprises a compound of formula III.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of formula III located on the second side of the insulator, and a drain electrode and a source electrode located on the polymer layer.

$C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_1$-$C_{25}$alkoxy ($C_1$-$C_{18}$alkoxy) groups are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of $C_1$-$C_8$alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably $C_1$-$C_4$alkoxy such as typically methoxy, ethoxy, n-propoxy, isopropoxy, n-butoxy, sec.-butoxy, isobutoxy, tert.-butoxy. The term "alkyithio group" means the same groups as the alkoxy groups, except that the oxygen atom of the ether linkage is replaced by a sulfur atom.

$C_2$-$C_{25}$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl ($C_{2-18}$alkynyl) is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn- 1-yl, 1,3-hexadiyn-5-yl, 1-octyn-8-yl, 1-nonyn-9-yl, 1-decyn-10-yl, or 1-tetracosyn-24-yl.

$C_5$-$C_{12}$cycloalkyl is typically cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with $C_1$-$C_4$-alkyl, halogen and cyano. Examples of such condensed cyclohexyl groups are:

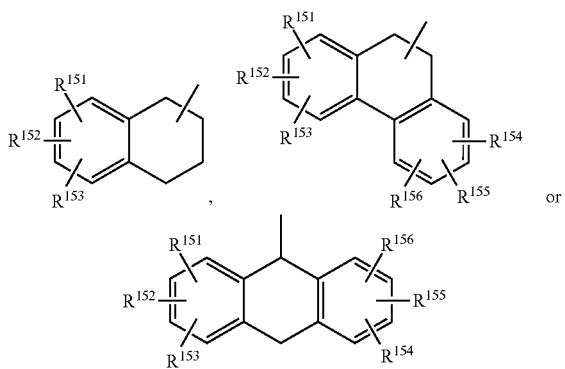

in particular

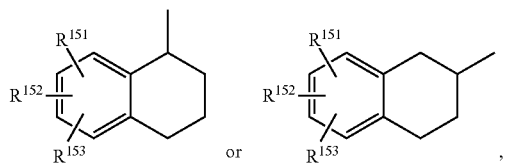

wherein $R^{151}$, $R^{152}$, $R^{153}$, $R^{154}$, $R^{155}$ and $R^{156}$ are independently of each other $C_1$-$C_8$-alkyl, $C_1$-$C_8$-alkoxy, halogen and cyano, in particular hydrogen.

$C_6$-$C_{24}$aryl is typically phenyl, indenyl, azulenyl, naphthyl, biphenyl, as-indacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of $C_6$-$C_{12}$aryl are phenyl, 1-naphthyl, 2-naphthyl, 3- or 4-biphenyl, 2- or 9-fluorenyl or 9-phenanthryl, which may be unsubstituted or substituted.

$C_7$-$C_{25}$aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably $C_7$-$C_{18}$aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred $C_7$-$C_{12}$aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

The term "carbamoyl group" is typically a $C_{1-18}$carbamoyl radical, preferably $C_{1-8}$carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

Heteroaryl is typically $C_2$-$C_{26}$heteroaryl ($C_2$-$C_{20}$heteroaryl), i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothlazinyl, isoxazolyl, furazanyl or phenoxazinyl, which can be unsubstituted or substituted.

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, a carbamoyl group, a nitro group or a silyl group, especially $C_1$-$C_8$alkyl, $C_1$-$C_8$alkoxy, $C_1$-$C_8$alkylthio, halogen, halo-$C_1$-$C_8$alkyl, or a cyano group.

As described above, the aforementioned groups may be substituted by E and/or, if desired, interrupted by D. Interruptions are of course possible only in the case of groups containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_{1-9}$—$R^x$, where $R^x$ is H or $C_1$-$C_{10}$alkyl or $C_2$-$C_{10}$alkanoyl (e.g. CO—CH($C_2H_5$)$C_4H_9$), $CH_2$—CH($OR^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR^z$, $CH(CH_3)COOR^z$, $C(CH_3)_2COOR^z$, where $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)CH_2$—O—CO—$C(CH_3)$=$CH_2$.

The following examples are included for illustrative purposes only and do not limit the scope of the claims. Unless otherwise stated, all parts and percentages are by weight. Weight-average molecular weight (Mw) and polydispersity (Mw/Mn=PD) are determined by High Temperature Gel Permeation Chromatography (HT-GPC) [Apparatus: GPC PL 220 from Polymer laboratories (Church Stretton, UK; now Varian) yielding the responses from refractive index (RI), Chromatographic conditions: Column: 3 "PLgel Olexis" column from Polymer Laboratories (Church Stretton, UK); with an average particle size of 13 μm (dimensions 300×8 mm I.D.) Mobile phase: 1,2,4-trichlorobenzene purified by vacuum distillation and stabilised by butylhydroxytoluene (BHT, 200 mg/l), Chromatographic temperature: 150° C.; Mobile phase flow: 1 ml/min; Solute concentration: about 1 mg/ml; Injection volume: 200 μl; Detection: RI, Procedure of molecular weight calibration: Relative calibration is done by use of a set of 10 polystyrene calibration standards obtained from Polymer Laboratories (Church Stretton, UK) spanning the molecular weight range from 1'930'000 Da-5'050 Da, i. e., PS 1'930'000, PS 1'460'000, PS All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1: Manufacture of the Semiconducting Compound of the Formula 5

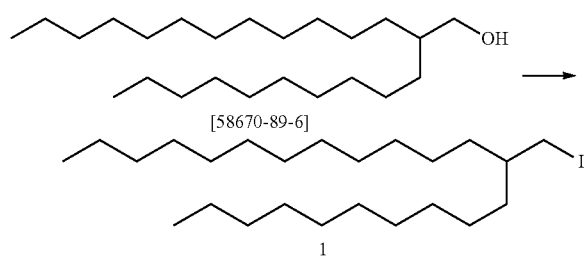

a) 228.06 g of 2-decyl-1-tetradecanol [58670-89-6] are mixed with 484.51 g 47% hydrolodic acid [10034-85-2] and the mixture is refluxed overnight. The product is extracted with t-butyl-methylether. Then the organic phase is dried and concentrated. The product is purified over a silica gel column to give 211.54 g of the desired compound 1 (73%). $^1$H-NMR data (ppm, CDCl$_3$): 3.26 2H d, 1.26-1.12 41H m, 0.88 6H t.

b) 5.70 g of the nitril [40985-58-8] are reacted with freshly prepared sodium t-amylate (170 ml t-amylalcohol, 2.22 g sodium and 10 mg FeCl$_3$) and 5.57 g di-tert-amylsuccinate (DTAS) over night at reflux. Precipitation of the crude DPP from acetic acid affords 5.6 g of the desired compound 2 (79%). MS m/z: 412.

c) 4 g of compound 2 and 5.6 g potassium carbonate in 200 ml of dimethylformamide are heated to 90° C. and then 11.82 g of the iodide 1 are added and the mixture is then stirred for 3 hours at 90° C. After cooling the reaction mixture is poured on water and the product is filtered and washed with water. Purification is achieved by column chromatography over silica gel and affords 1.7 g of the desired DPP 3 (15%). $^1$H-NMR data (ppm, CDCl$_3$): 9.30 2H s, 7.61 2H d, 7.33 2H d, 4.09 4H d, 2.01 2H m, 1.35-1.20 80H m, 0.89 6H t, 0.87 6H t.

d) 2.1 g 3 are dissolved in 40 ml of chloroform, cooled down to 0° C. and after the addition of a drop of perchloric acid 0.68 g of N-bromosuccinimide are then added portion wise over a period of 1 h. The reaction mixture is stirred at 0° C. After the reaction is completed, the mixture is washed with water. The organic phase is extracted, dried and concentrated. The compound is then purified over a silica gel column to give 2 g of the desired compound of the formula 4 (84%). $^1$H-NMR data (ppm, CDCl$_3$): 9.21 2H s, 7.33 2H s, 4.05 4H d, 1.97 2H m, 1.35-1.20 80H m, 0.89 6H t, 0.87 6H t.

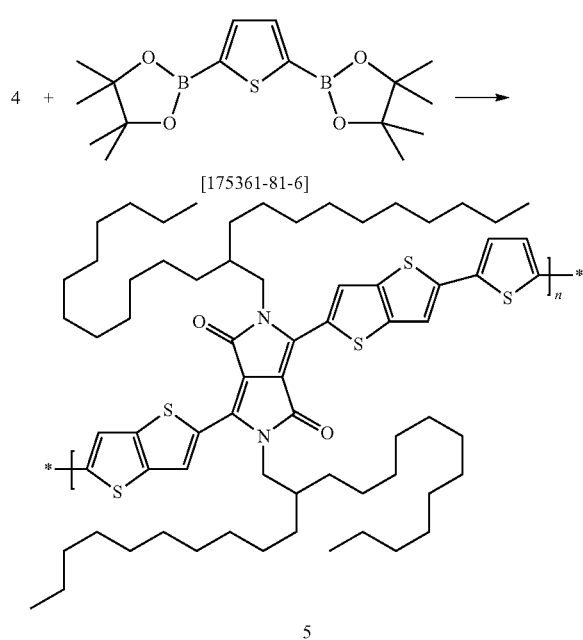

e) 810 mg of compound 4, 208 mg thiophene-di-boronic acid pinacol ester [175361-81-6], 15 mg Pd$_2$(dba)$_3$ (Tris(dibenzylideneacetone)-di-palladium) and 10 mg tri-tert-butyl-phosphonium-tetrafluoroborate are dissolved in 4 ml of tetrahydrofurane. This solution is degassed with 3 cycles of freeze/pump/thaw (Ar). The reaction mixture is then heated to reflux temperature. Then 418 mg of K$_3$PO$_4$ are dissolved in 1.2 ml of water and degassed under Argon. The water solution is added to the THF solution and the reaction mixture is refluxed over night. Then 14 mg of 2-thiophene-mono-boronic-acid-pinacol-ester [193978-23-3] are added, and the mixture is refluxed for another 30 minutes. Then 11 mg of 2-bromo-thiophene [1003-09-4] are added, and the mixture is refluxed for another 30 minutes. The reaction mixture is cooled to room temperature and diluted with water and then extracted with chloroforme. The chloroforme solution is then refluxed with a solution of NaCN in water for 1 hour. The water is separated and the chloroforme solution dried. The residue is then Soxhlet extracted with tetrahydrofurane. The organic phase is precipitated to give 635 mg of the desired polymer 5. Mw=38'000, Polydispersity=2.78 (measured by HT-GPC).

Example 2: Application of the Semiconducting Polymer of the Formula 5

The semiconductor thin film is prepared either by spin-coating the polymer of the formula 5 obtained in example 1 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and showed clear p-type transistor behavior. From a linear fit to the square root of the saturated transfer characteristics a field effect mobility of $5.6 \times 10^{-3}$ cm$^2$/Vs with an on/off current ratio of $3.5 \times 10^5$ can be determined.

Example 3: Photovoltaic Application of the Semiconducting Polymer of Formula 5 DPP-Monomer Based Bulk Heterojunction Solar Cell The solar cell has the following structure: Al electrode/LiF layer/organic layer, including compound of the invention/[poly(3,4-ethylenedioxy-thiophene) (PEDOT)/poly(styrenesulfonic acid) (PSS)]/ITO electrode/glass substrate. The solar cells are made by spin coating a layer of the PEDOT-PSS on a pre-patterned ITO on glass substrate. Then a 1:1 mixture of the polymer of formula 5 (1% by weight):[70]PCBM (a substituted C$_{70}$ fullerene) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions. This leads to a value of $J_{sc}$=2.4 mA/cm$^2$, FF=0.51 and $V_{oc}$=0.59 V for an estimated overall efficiency of 0.73%.

Example 4: Synthesis of Polymer 10

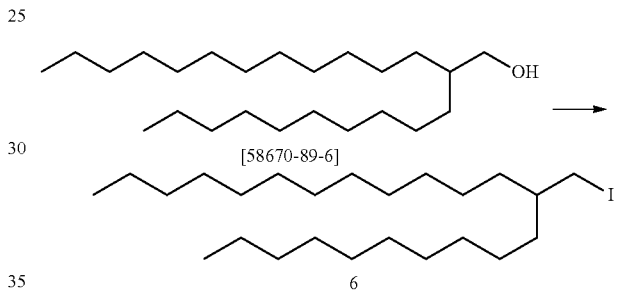

a) 228.06 g of 2-decyl-1-tetradecanol [58670-89-6] are mixed with 484.51 g 47% hydrolodic acid [10034-85-2] and the mixture is refluxed overnight. The product is extracted with t-butyl-methylether. Then the organic phase is dried and concentrated. The product is purified over a silica gel column to give 211.54 g of the desired compound 6 (73%). $^1$H-NMR data (ppm, CDCl$_3$): 3.26 2H d, 1.26-1.12 41H m, 0.88 6H t.

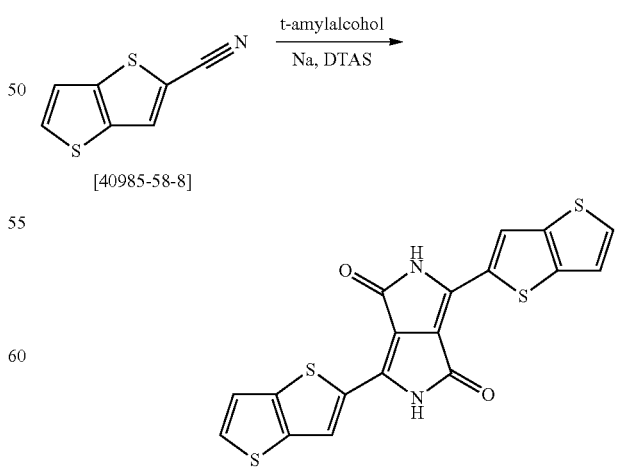

b) 5.70 g of the nitril [40985-58-8] are reacted with freshly prepared sodium t-amylate (170 ml t-amylalcohol, 2.22 g sodium and 10 mg $FeCl_3$) and 5.57 g di-tert-amylsuccinate (DTAS) over night at reflux. Precipitation of the crude DPP from acetic acid affords 5.6 g of the desired compound 7 (79%). MS m/z: 412.

6 + 7 ⟶

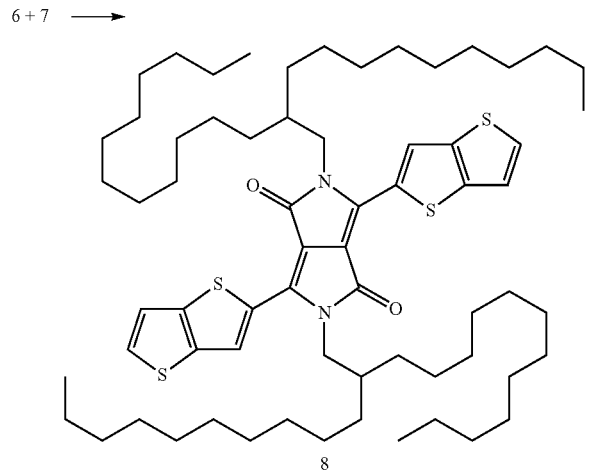

8 c) 4 g of compound 7 and 5.6 g potassium carbonate in 200 ml of dimethylformamide are heated to 90° C. and then 11.82 g of the iodide 6 are added and the mixture is then stirred for 3 hours at 90° C. After cooling the reaction mixture is poured on water and the product is filtered and washed with water. Purification is achieved by column chromatography over silica gel and affords 1.7 g of the desired DPP 8 (15%). $^1$H-NMR data (ppm, $CDCl_3$): 9.30 2H s, 7.61 2H d, 7.33 2H d, 4.09 4H d, 2.01 2H m, 1.35-1.20 80H m, 0.89 6H t, 0.87 6H t.

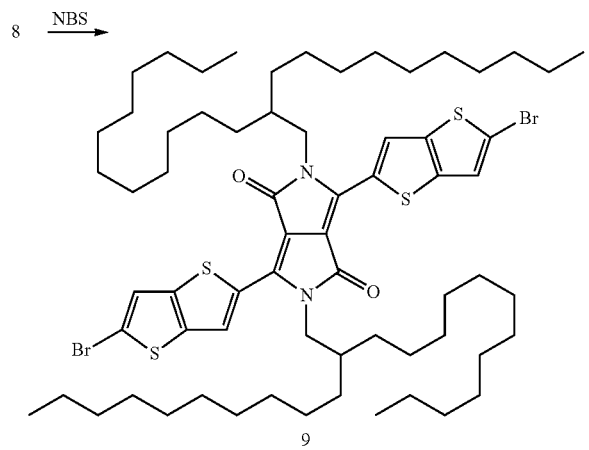

9 d) 2.1 g 8 are dissolved in 40 ml of chloroform, cooled down to 0° C. and after the addition of a drop of perchloric acid 0.68 g of N-bromosuccinimide are then added portion wise over a period of 1 h. The reaction mixture is stirred at 0° C. After the reaction is completed, the mixture is washed with water. The organic phase is extracted, dried and concentrated. The compound is then purified over a silica gel column to give 2 g of the desired compound of the formula 9 (84%). $^1$H-NMR data (ppm, $CDCl_3$): 9.21 2H s, 7.33 2H s, 4.05 4H d, 1.97 2H m, 1.35-1.20 80H m, 0.89 6H t, 0.87 6H t.

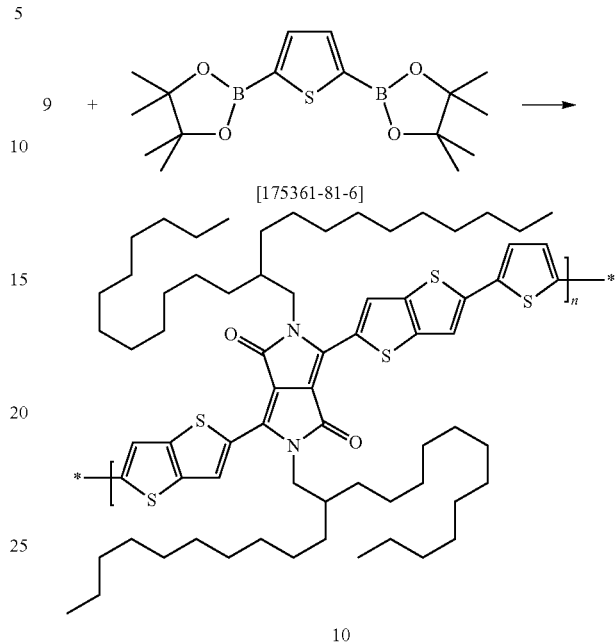

10 e) 810 mg of compound 9, 208 mg thiophene-di-boronic acid pinacol ester [175361-81-6], 15 mg $Pd_2(dba)_3$ (tris (dibenzylideneacetone)-di-palladium) and 10 mg tri-tert-butyl-phosphonium-tetrafluoroborate are dissolved in 4 ml of tetrahydrofurane. This solution is degassed with 3 cycles of freeze/pump/thaw (Ar). The reaction mixture is then heated to reflux temperature. Then 418 mg of $K_3PO_4$ are dissolved in 1.2 ml of water and degassed under Argon. The water solution is added to the THF solution and the reaction mixture is refluxed over night. Then 14 mg of 2-thiophene-mono-boronic-acid-pinacol-ester [193978-23-3] are added, and the mixture is refluxed for another 30 minutes. Then 11 mg of 2-bromo-thiophene [1003-09-4] are added, and the mixture is refluxed for another 30 minutes. The reaction mixture is cooled to room temperature and diluted with water and then extracted with chloroforme. The chloroforme solution is then refluxed with a solution of NaCN in water for 1 hour. The water is separated and the chloroforme solution dried. The residue is then Soxhlet extracted with tetrahydrofurane. The organic phase is precipitated to give 635 mg of the desired polymer 10. Mw=46'600, Polydispersity=2.72 (measured by HT-GPC).

Example 5: Synthesis of Compound 12

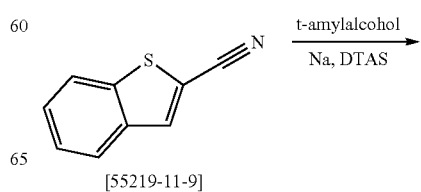

[55219-11-9]

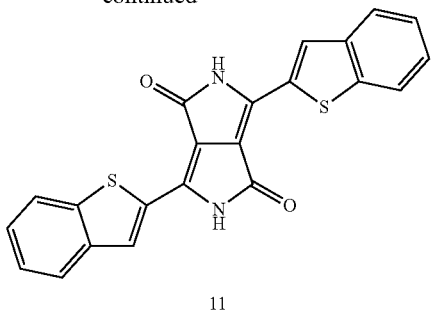

11 a) A mixture of 5 mg $FeCl_3$, 1.37 g sodium and 50 ml t-amylalcohol is heated to 110° C. for 30 minutes before a mixture of 3.5 g of nitrile [55219-11-9] and 2.76 g ditertamylsuccinate (DTAS) is added drop wise. The reaction mixture is stirred at 110° C. over night before it is poured onto a water-methanol mixture. Buchner filtration and exhaustive washing with methanol affords 3 g of the desired DPP derivative 11 as dark powder. MS m/z: 400.

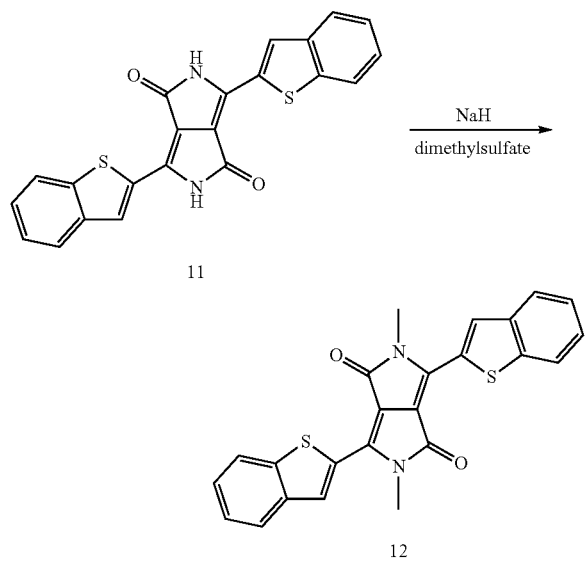

b) In 10 ml of dry dimethylformamide 1 g of compound 11 is suspended and 220 mg of sodiumhydride (60% in mineral oil) are added. The mixture is heated to 100° C. and then 1.86 g of dimethylsulfate is added and the mixture is stirred over night at 100° C. The crude product is poured on ice, filtered and washed with water. The product is recrystallized from dimethylformamide to give 0.63 g of a compound of formula 12. MS m/z: 428;

Example 6: Application of the Semiconducting Polymer 10

The semiconductor thin film is prepared by spin-coating the polymer 10 obtained in example 1 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zürich) and showed clear p-type transistor behavior. From a linear fit to the square root of the saturated transfer characteristics a field effect mobility of $5.6 \times 10^{-3}$ $cm^2/Vs$ with an on/off current ratio of $3.5 \times 10^5$ can be determined.

Example 7: Photovoltaic Application of the Semiconducting Polymer 10

The solar cell has the following structure: Al electrode/ LiF layer/organic layer, including compound of the invention/[poly(3,4-ethylenedioxy-thiophene) (PEDOT)/poly (styrenesulfonic acid) (PSS)]/ITO electrode/glass substrate. The solar cells are made by spin coating a layer of the PEDOT-PSS on a pre-patterned ITO on glass substrate. Then a 1:1 mixture of the polymer 10 (1% by weight): [70]PCBM (a substituted $C_{70}$ fullerene) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions. This leads to a value of $J_{sc}=2.4$ $mA/cm^2$, FF=0.51 and $V_{oc}=0.59$ V for an estimated overall efficiency of 0.73%.

The invention claimed is:
1. An organic semiconductor material, layer or component, comprising a polymer comprising one or more (repeating) unit(s) of the formula

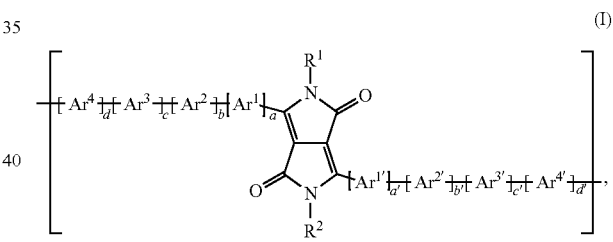

(I)

wherein a is 1, 2, or 3; a' is 0, 1, 2, or 3; b is 0, 1, 2, or 3; b' is 0, 1, 2, or 3; c is 0, 1, 2, or 3; c' is 0, 1, 2, or 3; d is 0, 1, 2, or 3; d' is 0, 1, 2, or 3; with the proviso that b' is not 0, if a' is 0;

$R^1$ and $R^2$ may be the same or different and are selected from hydrogen, a $C_1$-$C_{100}$alkyl group, —$COOR^{103}$, a $C_1$-$C_{100}$alkyl group which is substituted by one or more halogen atoms, hydroxyl groups, nitro groups, —CN, or $C_6$-$C_{18}$aryl groups and/or interrupted by —O—, —COO—, —OCO—, or —S—; a $C_7$-$C_{100}$arylalkyl group, which can be substituted one to three times with $C_1$-$C_8$alkyl and/or $C_1$-$C_8$alkoxy; a carbamoyl group, $C_5$-$C_{12}$cycloalkyl, which can be substituted one to three times with $C_1$-$C_8$alkyl and/or $C_1$-$C_8$alkoxy; a $C_6$-$C_{24}$aryl group, which can be substituted one to three times with $C_1$-$C_8$alkyl, $C_1$-$C_8$thioalkoxy, and/or $C_1$-$C_8$alkoxy, or pentafluorophenyl, $Ar^1$ and $Ar^{1'}$ are independently of each other an annulated (aromatic) heterocyclic ring system, containing at least one thiophene ring, which may be optionally substituted by one, or more groups, $Ar^2$, $Ar^{2'}$, $Ar^3$, $Ar^{3'}$, $Ar^4$ and $Ar^{4'}$ have the meaning of $Ar^1$, or are independently of each other

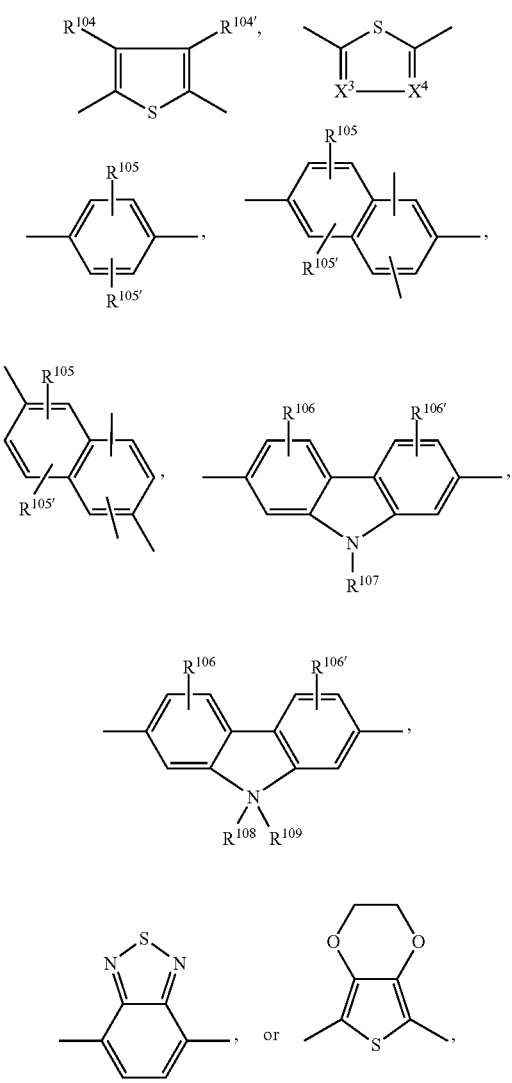

wherein one of $X^3$ and $X^4$ is N and the other is $CR^{99}$,
$R^{99}$, $R^{104}$ and $R^{104'}$ are independently of each other hydrogen, halogen, or a $C_1$-$C_{25}$alkyl group, which may optionally be interrupted by one or more oxygen or sulphur atoms, $C_7$-$C_{25}$arylalkyl, or a $C_1$-$C_{25}$alkoxy group, $R^{105}$, $R^{105'}$, $R^{106}$ and $R^{106'}$ are independently of each other hydrogen, halogen, $C_1$-$C_{25}$alkyl, which may optionally be interrupted by one or more oxygen or sulphur atoms;
$C_7$-$C_{25}$arylalkyl, or $C_1$-$C_{18}$alkoxy,
$R^{107}$ is $C_7$-$C_{25}$arylalkyl, $C_6$-$C_{18}$aryl; $C_6$-$C_{18}$aryl which is substituted by $C_1$-$C_{18}$alkyl, $C_1$-$C_{18}$perfluoroalkyl, or $C_1$-$C_{18}$alkoxy; $C_1$-$C_{18}$alkyl; $C_1$-$C_{18}$alkyl which is interrupted by —O—, or —S—; or —COOR$^{103}$; $R^{103}$ is $C_1$-$C_{50}$alkyl;
$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or
$R^{108}$ and $R^{109}$ together form a group of formula =$CR^{110}R^{111}$, wherein
$R^{110}$ and $R^{111}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D,
$C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl,
D is —CO—, —COO—, —S—, —O—, or —NR$^{112}$—,
E is $C_1$-$C_8$thioalkoxy, $C_1$-$C_8$alkoxy, CN, —NR$^{112}$R$^{113}$, —CONR$^{112}$R$^{113}$, or halogen,
G is E, or $C_1$-$C_{18}$alkyl, and
$R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—.

2. The organic semiconductor material, layer or component comprising a polymer according to claim 1, wherein the polymer comprises one or more (repeating) unit(s) of the formula (Ia)

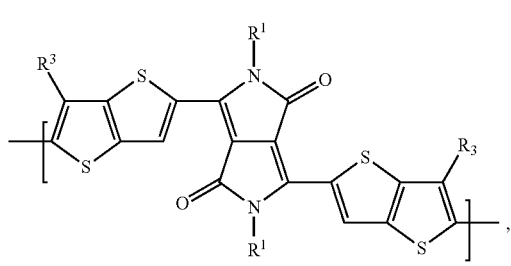

(Ib)

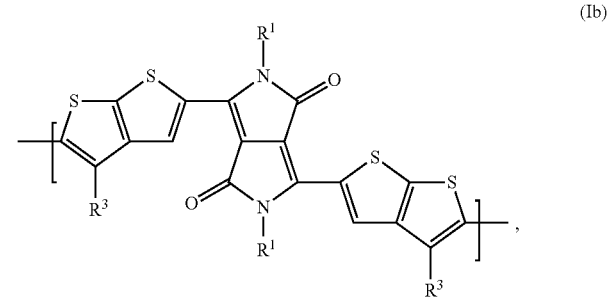

(Ic)
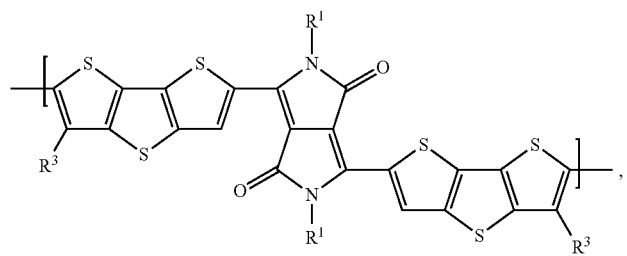
(Id)
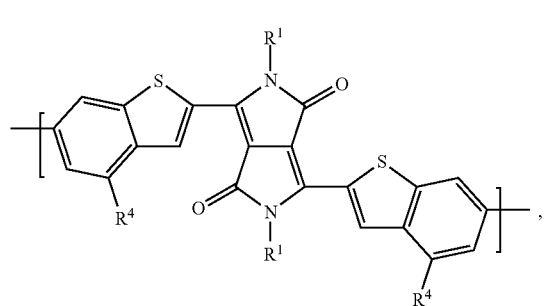
(Ie)
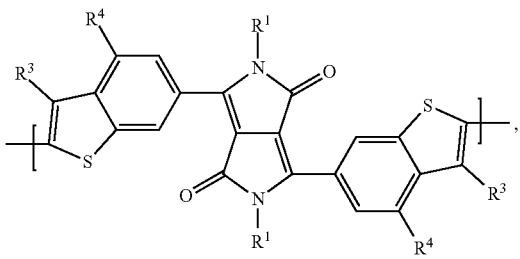
(If)
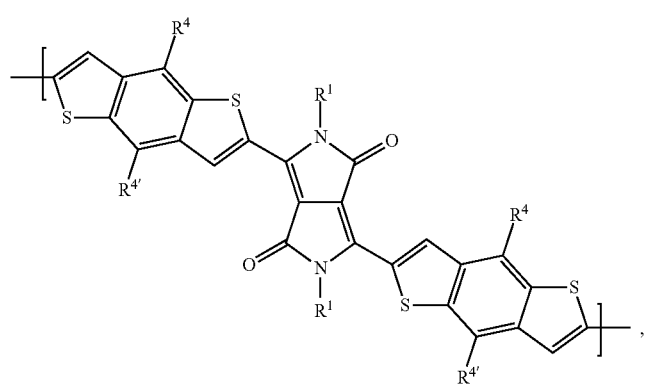
(Ig)
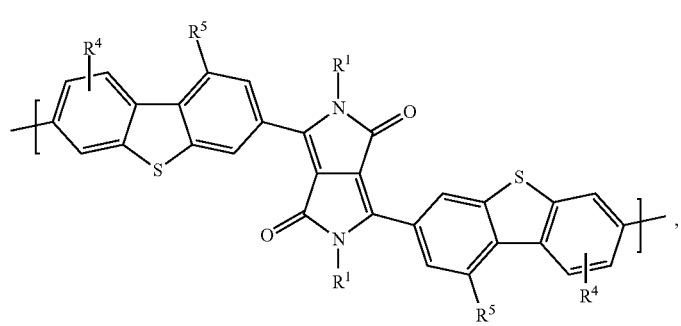

-continued
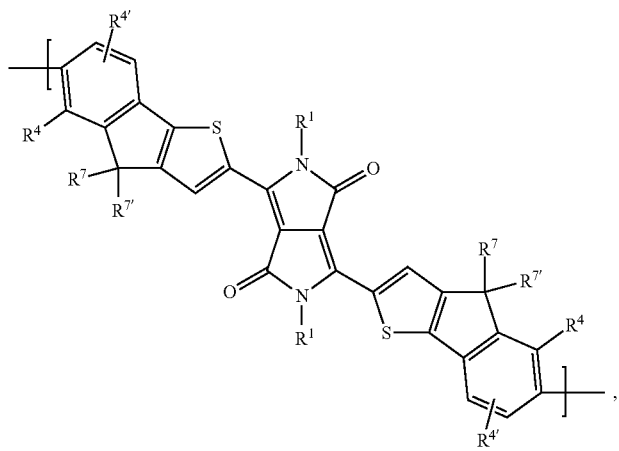
(Ih)
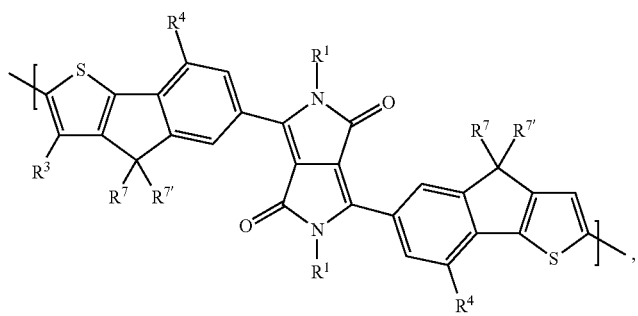
(Ii)
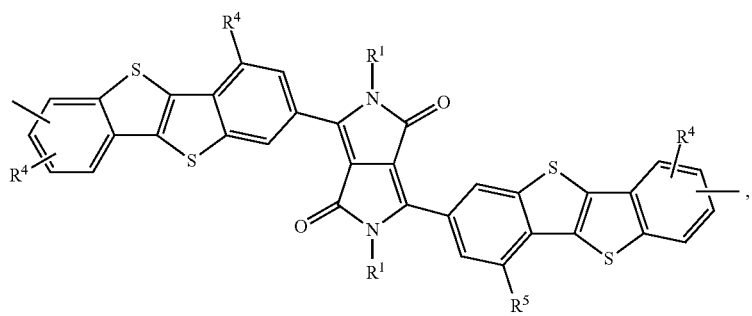
(Ij)
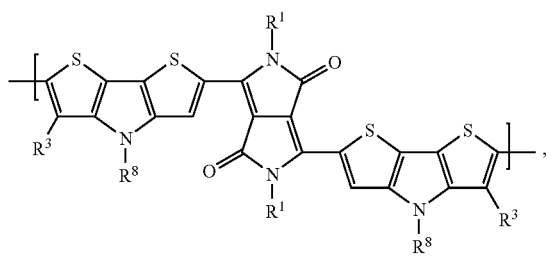
(Ik)
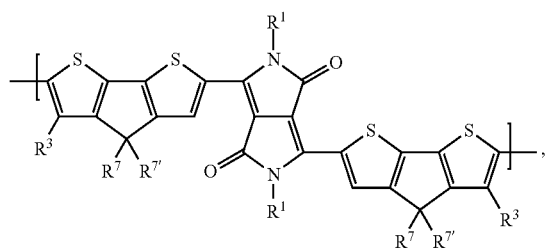
(Il)
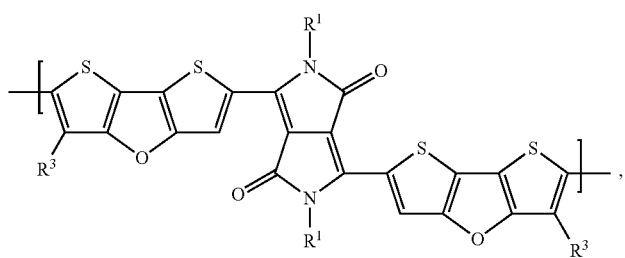
(Im)

(In)
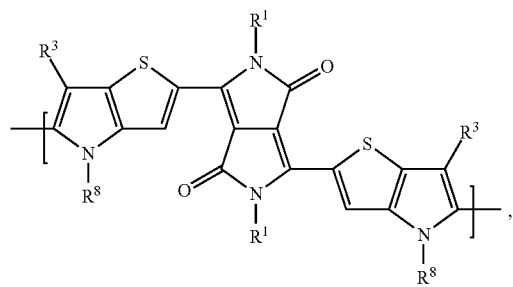
(Io)
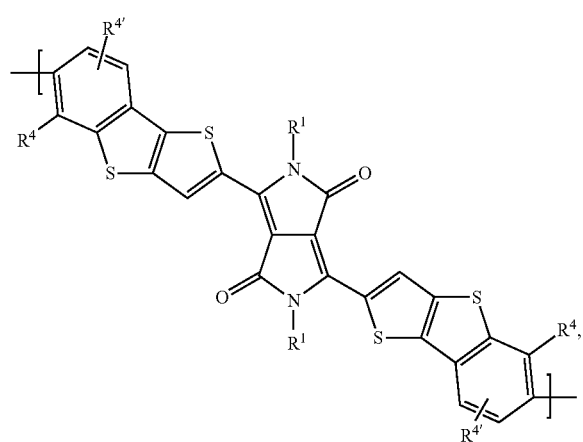
(Ip)
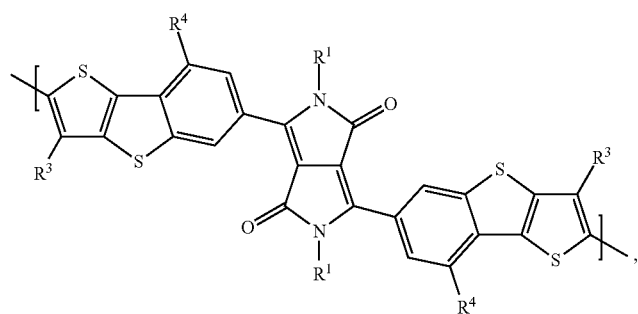
(Iq)
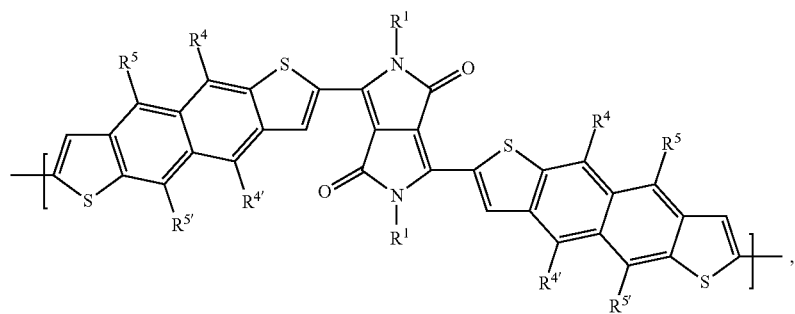

-continued
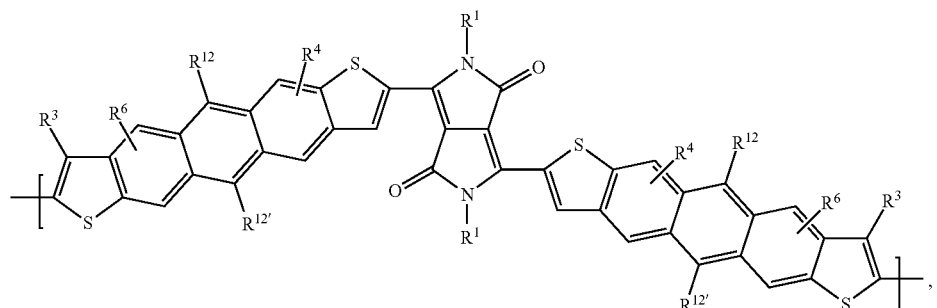
(Ir)
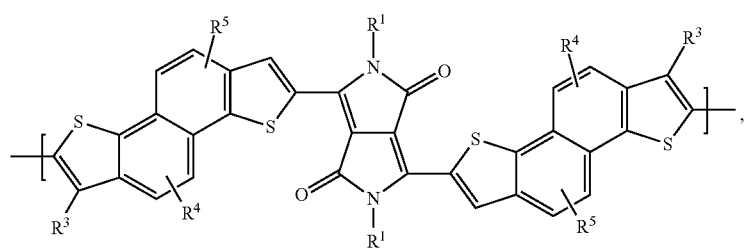
(Is)
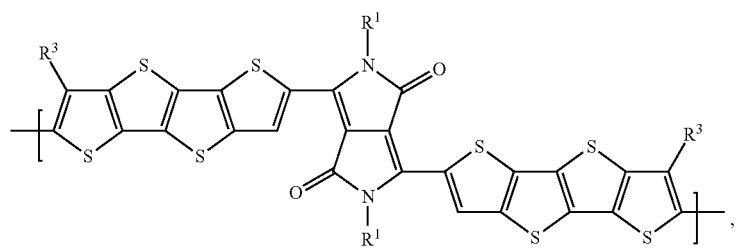
(It)
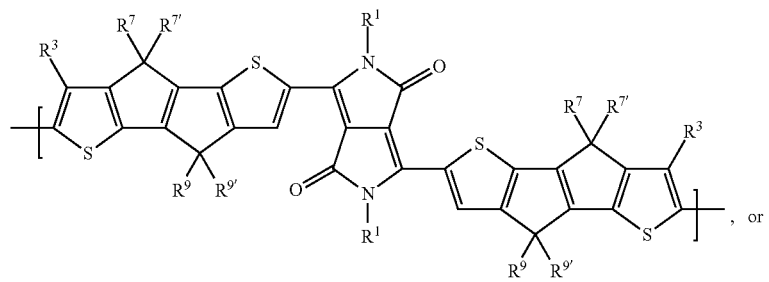
(Iu)
, or
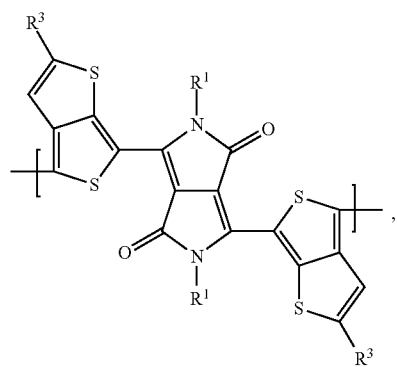
(Iv)

wherein
R¹ is a $C_8$-$C_{36}$alkyl group,
R³ is hydrogen, halogen, $C_1$-$C_{25}$alkyl, which may optionally be interrupted by one or more oxygen or sulphur atoms, $C_7$-$C_{25}$aralkyl, or $C_1$-$C_{25}$alkoxy;
R⁴, R⁴', R⁵, R⁵' and R⁶ are independently of each other hydrogen, halogen, $C_1$-$C_{25}$alkyl, which may optionally be interrupted by one or more oxygen or sulphur atoms, $C_7$-$C_{25}$aralkyl, or $C_1$-$C_{25}$alkoxy;
R⁷, R⁷', R⁹ and R⁹' are independently of each other hydrogen, $C_1$-$C_{25}$alkyl, which may optionally be interrupted by one, or more oxygen, or sulphur atoms, or $C_7$-$C_{25}$aralkyl,
R⁸ is $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms, and
R¹² and R¹²' are independently of each other hydrogen, halogen, $C_1$-$C_{25}$alkyl, which may optionally be interrupted by one, or more oxygen, or sulphur atoms, $C_1$-$C_{25}$alkoxy, or

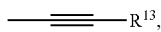

wherein R¹³ is $C_1$-$C_{10}$alkyl group, or a tri($C_1$-$C_8$alkyl)silyl group.

3. The organic semiconductor material, layer or component according to claim 1, wherein the polymer comprises (repeating) unit(s) of the formula

(II)

wherein
A is a repeating unit of formula (I), and
COM¹- is a repeating unit, which is selected from a group of formula Ar¹, such as, for example,

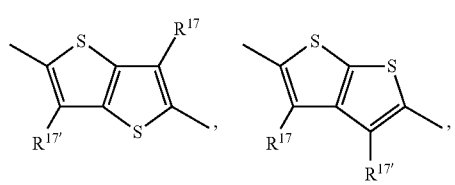

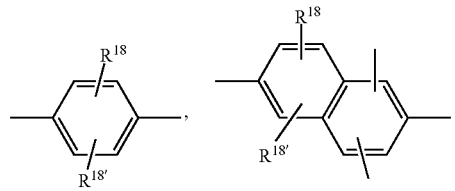

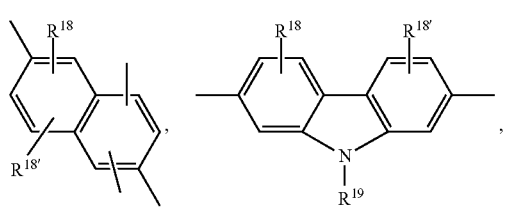

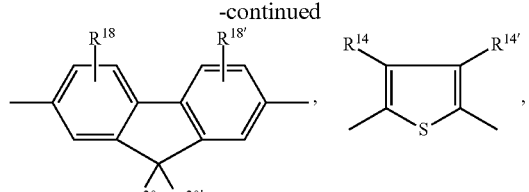

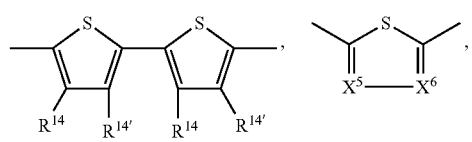

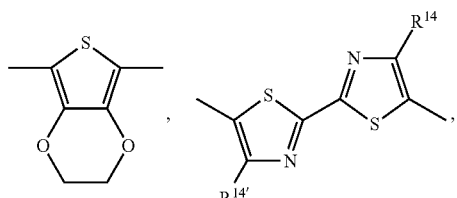

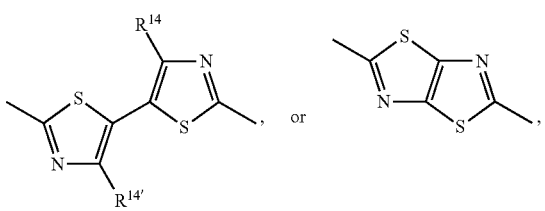

wherein
one of X⁵ and X⁶ is N and the other is CR¹⁴
R¹⁴, R¹⁴', R¹⁷ and R¹⁷' are independently of each other hydrogen, halogen, $C_1$-$C_{25}$alkyl, which may optionally be interrupted by one or more oxygen or sulphur atoms, $C_7$-$C_{25}$aralkyl, or $C_1$-$C_{25}$alkoxy;
R¹⁸ and R¹⁸' independently of each other hydrogen, halogen, $C_1$-$C_{25}$alkyl, which may optionally be interrupted by one or more oxygen or sulphur atoms, $C_7$-$C_{25}$aralkyl, or $C_1$-$C_{25}$alkoxy;
R¹⁹ is hydrogen, $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms;
R²⁰ and R²⁰' are independently of each other hydrogen, $C_7$-$C_{25}$aralkyl, $C_1$-$C_{25}$alkyl, which may optionally be interrupted by one, or more oxygen, or sulphur atoms, and Ar¹ is as defined in claim 1.

4. The organic semiconductor material, layer or component according to claim 3, wherein A is a repeating unit of formula (Ia), (Ib), (Ic), (Id), (Ie), (If), (Ig), (Ih), (Ii), (Ij), (Ik), (Il), (Im), (In), (Io), (Ip), (Iq), (Ir), (Is), (It), (Iu) or (Iv) as defined in claim 2.

5. The organic semiconductor material, layer or component according to claim 3, wherein the polymer comprises one or more (repeating) unit(s) of the formula

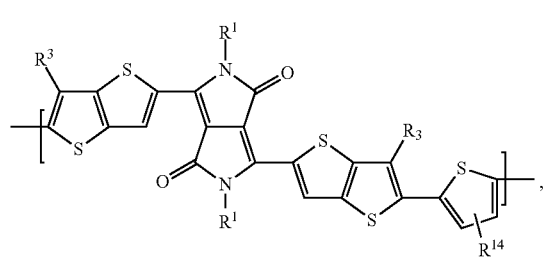
(IIa)
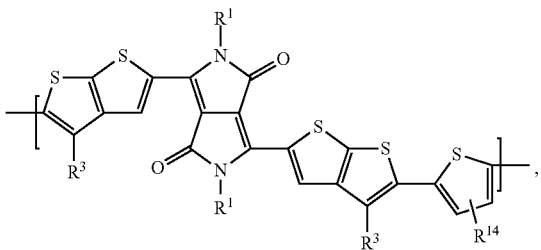
(IIb)
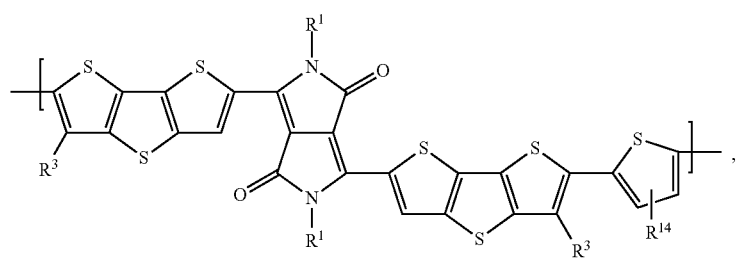
(IIc)
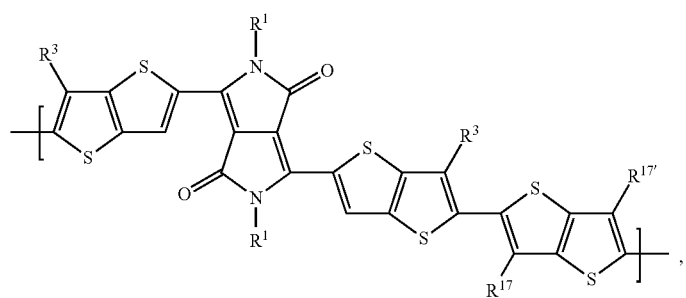
(IId)
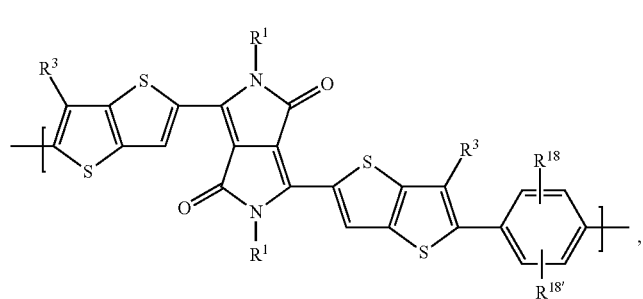
(IIe)
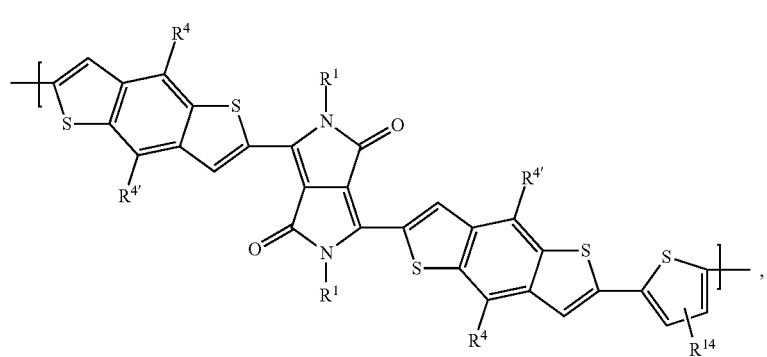
(IIf)

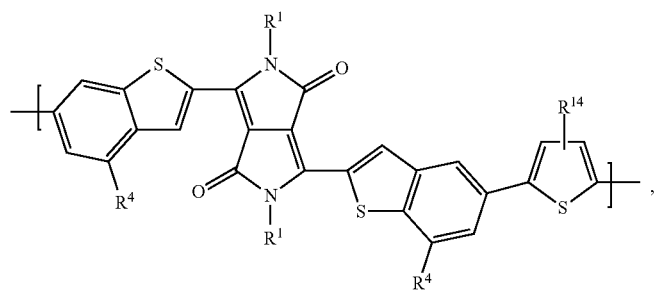
(IIg)
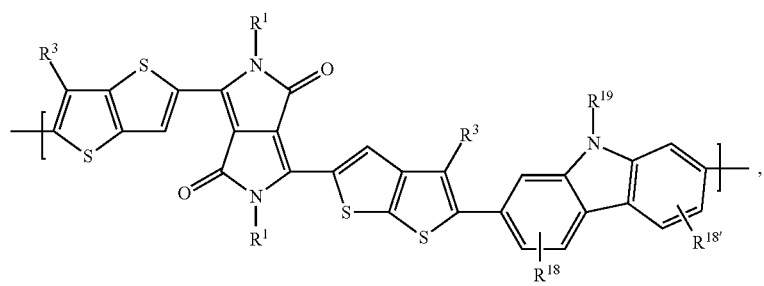
(IIh)
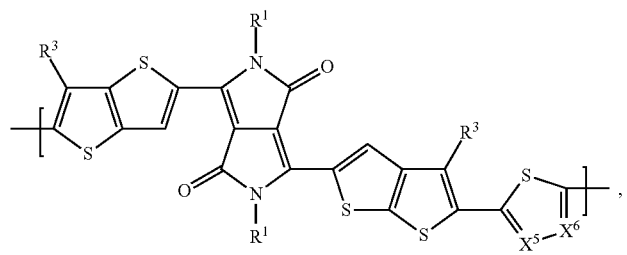
(IIi)
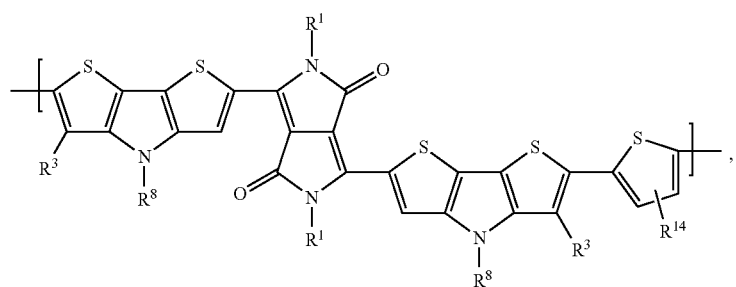
(IIj)
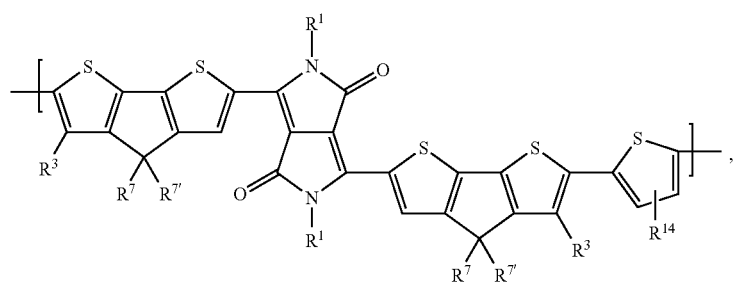
(IIk)

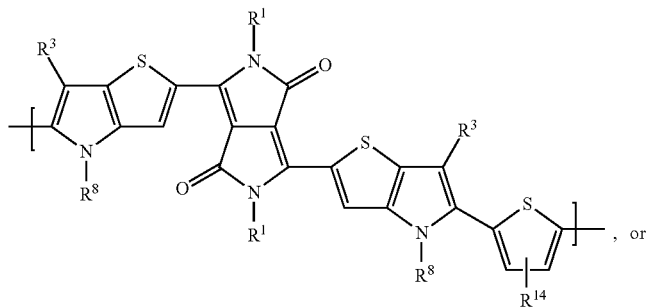
(III)

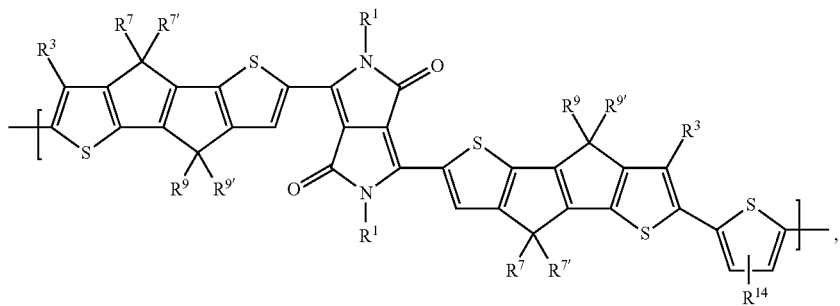
(IIm)

- $R^1$ is a $C_8$-$C_{36}$alkyl group,
- $R^3$ is hydrogen, halogen, $C_1$-$C_{25}$alkyl, which may optionally be interrupted by one or more oxygen or sulphur atoms, $C_7$-$C_{25}$aralkyl, or $C_1$-$C_{25}$alkoxy; $R^4$, $R^{4'}$ and $R^5$ are independently of each other hydrogen, halogen, $C_1$-$C_{25}$alkyl, which may optionally be interrupted by one or more oxygen or sulphur atoms, $C_7$-$C_{25}$aralkyl, or $C_1$-$C_{25}$alkoxy;
- $R^7$, $R^{7'}$, $R^9$ and $R^{9'}$ are independently of each other hydrogen, $C_1$-$C_{25}$alkyl, which may optionally be interrupted by one, or more oxygen, or sulphur atoms; or $C_7$-$C_{25}$aralkyl,
- $R^8$ is $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms;
- $R^{19}$ is $C_7$-$C_{25}$aralkyl, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms,
- one of $X^5$ and $X^6$ is N and the other is $CR^{14}$,
- $R^{14}$, $R^{14'}$, $R^{17}$ and $R^{17'}$ are independently of each other hydrogen, halogen, $C_1$-$C_{25}$alkyl, $C_1$-$C_{25}$alkoxy, which may optionally be interrupted by one or more oxygen or sulphur atoms; or $C_7$-$C_{25}$aralkyl,
- $R^{18}$ and $R^{18'}$ independently of each other hydrogen, halogen, $C_1$-$C_{25}$alkyl, which may optionally be interrupted by one or more oxygen or sulphur atoms; $C_7$-$C_{25}$aralkyl, or $C_1$-$C_{25}$alkoxy.

* * * * *